(12) United States Patent
Terrill et al.

(10) Patent No.: US 9,610,168 B2
(45) Date of Patent: Apr. 4, 2017

(54) TOTAL ANKLE REPLACEMENT PROSTHESIS

(71) Applicant: Integra LifeSciences Corporation, Plainsboro, NJ (US)

(72) Inventors: Lance Terrill, Oviedo, FL (US); Shawn Roman, Oviedo, FL (US); Timothy R. Daniels, Toronto, CA (US); Christopher F. Hyer, Columbus, OH (US); Selene G. Parekh, Cary, NC (US); David I. Pedowitz, Penn Valley, PA (US)

(73) Assignee: Integra LifeSciences Corporation, Plainsboro, NJ (US)

( * ) Notice: Subject to any disclaimer, the term of this patent is extended or adjusted under 35 U.S.C. 154(b) by 0 days.

(21) Appl. No.: 14/710,450

(22) Filed: May 12, 2015

(65) Prior Publication Data
US 2015/0320567 A1    Nov. 12, 2015

Related U.S. Application Data

(60) Provisional application No. 61/991,880, filed on May 12, 2014.

(51) Int. Cl.
*A61F 2/42* (2006.01)

(52) U.S. Cl.
CPC .... *A61F 2/4202* (2013.01); *A61F 2002/4205* (2013.01); *A61F 2002/4207* (2013.01); *A61F 2220/0033* (2013.01)

(58) Field of Classification Search
CPC ............ A61F 2/4202; A61F 2002/4205; A61F 2002/4207; A61F 2002/30884
See application file for complete search history.

(56) References Cited

U.S. PATENT DOCUMENTS 3,872,519 A    3/1975  Goiannestras et al.
3,987,500 A    10/1976 Schlein
(Continued)

FOREIGN PATENT DOCUMENTS

DE    8812806     1/1989
DE    19949890    6/2001
(Continued)

OTHER PUBLICATIONS

European Patent Office, International Search Report from PCT/US2015/030418 dated Jun. 29, 2015 Jun. 29, 2015, Rijswijk, Netherlands.
(Continued)

*Primary Examiner* — Brian Dukert
(74) *Attorney, Agent, or Firm* — Middleton Reutlinger; Robert H. Eichenberger; Chad D. Bruggeman

(57) ABSTRACT

A total ankle replacement prosthesis may comprise a tibial implant, a talar implant, and an intermediate implant. The intermediate implant may fixedly attach to the tibial implant and may articulate with respect to the talar implant. The intermediate implant may have unequal front and back angular extent, so as to discourage a particular direction of subluxation, and a kit may be provided containing various such intermediate implants. Various features may be provided in regard to dovetails, fins, recesses, the placement of fins and pegs, and the shape of the perimeter of the tibial implant. Recesses may allow a surgical blade to slice a latch off of an already-installed intermediate implant, in order to allow its removal from the tibial implant.

29 Claims, 17 Drawing Sheets

(56) References Cited

U.S. PATENT DOCUMENTS

| | | | |
|---|---|---|---|
| 4,309,778 A | 1/1982 | Buechel et al. | |
| 4,340,978 A | 7/1982 | Buechel et al. | |
| 4,759,766 A | 7/1988 | Buettner-Janz et al. | |
| 4,952,213 A | 8/1990 | Bowman et al. | |
| 4,986,833 A * | 1/1991 | Worland | A61F 2/4081 623/19.11 |
| 5,019,103 A | 5/1991 | Van Zile et al. | |
| 5,108,442 A | 4/1992 | Smith | |
| 5,137,536 A | 8/1992 | Koshino | |
| 5,203,807 A | 4/1993 | Evans et al. | |
| 5,246,459 A | 9/1993 | Elias | |
| 5,326,365 A | 7/1994 | Alvine | |
| 5,653,714 A | 8/1997 | Dietz et al. | |
| 5,681,320 A | 10/1997 | McGuire | |
| 5,681,354 A | 10/1997 | Eckhoff | |
| 5,702,463 A | 12/1997 | Pothier et al. | |
| 5,702,464 A | 12/1997 | Lackey et al. | |
| 5,716,361 A | 2/1998 | Masini | |
| 5,766,256 A | 6/1998 | Oudard et al. | |
| 5,766,259 A | 6/1998 | Sammarco | |
| 5,824,106 A | 10/1998 | Fournol | |
| 5,911,724 A | 6/1999 | Wehrli | |
| 6,010,534 A | 1/2000 | O'Neil et al. | |
| 6,102,954 A | 8/2000 | Albrektsson et al. | |
| 6,126,692 A | 10/2000 | Robie et al. | |
| 6,168,629 B1 | 1/2001 | Timoteo | |
| 6,183,519 B1 * | 2/2001 | Bonnin | A61F 2/4202 623/21.11 |
| 6,258,126 B1 | 7/2001 | Colleran | |
| 6,261,322 B1 | 7/2001 | Despres, III et al. | |
| 6,299,646 B1 | 10/2001 | Chambat et al. | |
| 6,312,475 B1 | 11/2001 | Voisin | |
| 6,402,785 B1 | 6/2002 | Zdeblick et al. | |
| 6,409,767 B1 | 6/2002 | Pericë et al. | |
| 6,488,712 B1 | 12/2002 | Tornier et al. | |
| 6,540,786 B2 | 4/2003 | Chibrac et al. | |
| 6,569,202 B2 | 5/2003 | Whiteside | |
| 6,595,997 B2 | 7/2003 | Axelson, Jr. et al. | |
| 6,652,588 B2 | 11/2003 | Hayes, Jr. et al. | |
| 6,663,669 B1 | 12/2003 | Reiley | |
| 6,673,116 B2 | 1/2004 | Reiley | |
| 6,709,461 B2 | 3/2004 | O'Neil et al. | |
| 6,824,567 B2 | 11/2004 | Tornier et al. | |
| 6,852,130 B2 | 2/2005 | Keller et al. | |
| 6,858,032 B2 | 2/2005 | Chow et al. | |
| 6,860,902 B2 | 3/2005 | Reiley | |
| 6,863,691 B2 | 3/2005 | Short et al. | |
| 6,875,236 B2 | 4/2005 | Reiley | |
| 6,926,739 B1 | 8/2005 | O'Connor et al. | |
| 6,939,380 B2 | 9/2005 | Guzman | |
| 6,962,607 B2 | 11/2005 | Gundlapalli et al. | |
| 6,966,928 B2 | 11/2005 | Fell et al. | |
| 7,011,687 B2 | 3/2006 | Deffenbaugh et al. | |
| 7,025,790 B2 | 4/2006 | Parks et al. | |
| 7,029,477 B2 | 4/2006 | Grimm | |
| 7,056,344 B2 | 6/2006 | Huppert et al. | |
| 7,101,401 B2 | 9/2006 | Brack | |
| 7,172,597 B2 | 2/2007 | Sanford | |
| 7,189,262 B2 | 3/2007 | Hayes, Jr. | |
| 7,314,488 B2 | 1/2008 | Reiley | |
| 7,323,012 B1 | 1/2008 | Stone et al. | |
| 7,476,227 B2 | 1/2009 | Tornier et al. | |
| 7,485,147 B2 | 2/2009 | Pappas et al. | |
| 7,513,912 B2 | 4/2009 | Hayes, Jr. et al. | |
| 7,534,270 B2 | 5/2009 | Ball | |
| 7,544,211 B2 | 6/2009 | Rochetin | |
| 7,578,850 B2 | 8/2009 | Kuczynski et al. | |
| 7,621,920 B2 | 11/2009 | Claypool et al. | |
| 7,625,409 B2 | 12/2009 | Saltzman et al. | |
| 7,628,818 B2 | 12/2009 | Hazebrouck et al. | |
| 7,635,390 B1 | 12/2009 | Bonutti | |
| 7,641,661 B2 | 1/2010 | Steffensmeier et al. | |
| 7,641,697 B2 | 1/2010 | Reiley | |
| 7,717,920 B2 | 5/2010 | Reiley | |
| 7,771,483 B2 | 8/2010 | Justin et al. | |
| 7,794,467 B2 | 9/2010 | McGinley et al. | |
| 7,833,287 B2 | 11/2010 | Doddroe et al. | |
| 7,867,279 B2 | 1/2011 | Hester et al. | |
| 7,892,262 B2 | 2/2011 | Rhoda et al. | |
| 7,901,462 B2 | 3/2011 | Yang et al. | |
| 7,951,204 B2 | 5/2011 | Chambat et al. | |
| 7,963,969 B2 | 6/2011 | Sanford | |
| 7,963,996 B2 | 6/2011 | Saltzman et al. | |
| 7,993,346 B2 | 8/2011 | Tornier et al. | |
| 8,002,777 B2 | 8/2011 | Fox et al. | |
| 8,002,839 B2 | 8/2011 | Rochetin | |
| 8,002,841 B2 | 8/2011 | Hasselman | |
| 8,012,212 B2 | 9/2011 | Link et al. | |
| 8,012,216 B2 | 9/2011 | Metzger | |
| 8,012,217 B2 | 9/2011 | Strzepa et al. | |
| 8,034,114 B2 | 10/2011 | Reiley | |
| 8,034,115 B2 | 10/2011 | Reiley | |
| 8,048,164 B2 | 11/2011 | Reiley | |
| 8,105,386 B2 | 1/2012 | Perrone, Jr. et al. | |
| 8,114,091 B2 | 2/2012 | Ratron et al. | |
| 8,118,873 B2 | 2/2012 | Humphreys et al. | |
| 8,118,875 B2 | 2/2012 | Rollet | |
| 8,128,703 B2 | 3/2012 | Hazebrouck et al. | |
| 8,142,505 B2 | 3/2012 | Tauber | |
| 8,142,510 B2 | 3/2012 | Lee et al. | |
| 8,157,868 B2 | 4/2012 | Walker et al. | |
| 8,167,948 B2 | 5/2012 | Paul et al. | |
| 8,211,113 B2 | 7/2012 | Brown et al. | |
| 8,287,601 B2 | 10/2012 | Wagner et al. | |
| 8,303,667 B2 | 11/2012 | Younger | |
| 8,317,870 B2 | 11/2012 | Wagner et al. | |
| 8,337,503 B2 | 12/2012 | Lian | |
| 8,460,303 B2 | 6/2013 | Park | |
| 8,470,047 B2 | 6/2013 | Hazebrouck et al. | |
| 8,480,755 B2 | 7/2013 | Reiley | |
| 8,568,486 B2 | 10/2013 | Wentorf et al. | |
| 8,574,304 B2 | 11/2013 | Wentorf et al. | |
| 8,591,595 B2 | 11/2013 | Kofoed et al. | |
| 8,591,596 B2 | 11/2013 | Long | |
| 8,603,101 B2 | 12/2013 | Claypool et al. | |
| 8,613,775 B2 | 12/2013 | Wentorf et al. | |
| 8,617,250 B2 | 12/2013 | Metzger | |
| 8,628,580 B2 | 1/2014 | Sanford et al. | |
| 8,632,600 B2 | 1/2014 | Zannis et al. | |
| 8,715,363 B2 | 5/2014 | Ratron et al. | |
| 2003/0083747 A1 | 5/2003 | Winterbottom et al. | |
| 2003/0181985 A1 | 9/2003 | Keller et al. | |
| 2004/0002768 A1 | 1/2004 | Parks et al. | |
| 2004/0030399 A1 | 2/2004 | Asencio | |
| 2004/0133282 A1 | 7/2004 | Deffenbaugh et al. | |
| 2005/0004676 A1 | 1/2005 | Schron et al. | |
| 2005/0043802 A1 | 2/2005 | Eisermann et al. | |
| 2005/0085917 A1 * | 4/2005 | Marnay | A61F 2/4425 623/17.16 |
| 2005/0288792 A1 | 12/2005 | Landes et al. | |
| 2006/0020345 A1 * | 1/2006 | O'Connor | A61F 2/4606 623/21.18 |
| 2006/0036325 A1 | 2/2006 | Paul et al. | |
| 2006/0116768 A1 | 6/2006 | Krueger et al. | |
| 2006/0142870 A1 | 6/2006 | Robinson et al. | |
| 2006/0229730 A1 * | 10/2006 | Railey | A61B 17/15 623/21.18 |
| 2006/0247788 A1 | 11/2006 | Ross | |
| 2008/0097617 A1 | 4/2008 | Fellinger et al. | |
| 2008/0103603 A1 | 5/2008 | Hintermann | |
| 2008/0109081 A1 | 5/2008 | Bao et al. | |
| 2008/0195233 A1 | 8/2008 | Ferrari et al. | |
| 2009/0054992 A1 | 2/2009 | Landes et al. | |
| 2011/0035019 A1 | 2/2011 | Goswami et al. | |
| 2011/0276052 A1 | 11/2011 | Hasselman | |
| 2012/0109326 A1 * | 5/2012 | Perler | A61F 2/4202 623/21.18 |
| 2012/0271430 A1 | 10/2012 | Arnett | |
| 2013/0041473 A1 | 2/2013 | Rouyer et al. | |
| 2013/0046313 A1 * | 2/2013 | Lian | A61B 17/92 606/99 |

(56) References Cited

U.S. PATENT DOCUMENTS

2013/0116797 A1   5/2013   Coulange et al.
2015/0238320 A1   8/2015   Ferrari et al.

FOREIGN PATENT DOCUMENTS

| EP | 2124832 A2 | 12/2009 |
| EP | 2316384 A1 | 5/2011 |
| EP | 1915975 | 4/2012 |
| EP | 2649966 | 10/2013 |
| EP | 2679173 | 1/2014 |
| FR | 2724108 | 3/1996 |
| FR | 2905259 | 3/2008 |
| GB | 19949890 A1 | 6/2001 |
| GB | 2477661 A | 8/2011 |
| JP | 2013526971 | 6/2013 |
| WO | 2012018564 | 2/2012 |
| WO | 2012061453 | 5/2012 |
| WO | 2013153435 | 10/2013 |

OTHER PUBLICATIONS

History of Continuous Innovation, Inbone and Infinity Total Ankle System, Wright Focused Excellence, Jan. 14, 2014.
Zimmer® Trabecular Metal™ Total Ankle Surgical Technique, Zimmer Personal Fit. Renewed Life™ 2012.

\* cited by examiner

TOTAL ANKLE REPLACEMENT PROSTHESIS

CLAIM TO PRIORITY

This utility patent application claims priority to the U.S. Provisional Patent Application Ser. No. 61/991,880, filed on May 12, 2014, the entire contents of which are hereby incorporated by reference.

BACKGROUND

Field

The present disclosure generally relates to systems and methods for replacement of an ankle by a prosthesis.

Description of the Related Art

Patients with certain types of ankle problems may require a total ankle replacement prosthesis. Although such devices have been used for some time, improvements are still needed in various respects, including but not limited to features that contribute to ease of implantation by a surgeon, resistance to posterior separation post-operatively, and resistance to component subsidence.

SUMMARY

Embodiments of the invention address many of the problems encountered with prostheses for various anatomical joints, including but not limited to, total ankle replacement prostheses. Many of the features of these embodiments are particularly helpful when employed using an anterior approach, as opposed to a medial-lateral approach. Posterior separation resistance is aided with the use of a wedge entirely or partially on the posterior side of the tibial component. One or more pegs can be used to provide guidance for the wedge. Preferably the surgical technique involves no bone preparation beyond initial saw cutting, although preparation for the wedge or the pegs, or both, are possible. Component subsidence resistance is aided by minimizing bone resection and by maximizing the extent that the components rest on cortical bone rim. Embodiments utilize a lateral flare to cover the anterior cortical rim of the tibia, as opposed to traditional trapezoidal or oblong footprints found in many prior art designs. This lateral flare increases the contact area of the tibial tray with the cortical rim of the anterior tibia. The lateral flare follows the anatomic tibia shape in the transverse plane by wrapping around the anterior aspect of the fibula.

An embodiment of the invention comprises a tibial implant, a talar implant and an intermediate implant, wherein the intermediate implant fixedly attaches to the tibial implant and is capable of articulating with respect to the talar implant, wherein the intermediate implant has a first edge of the articulating surface and a second edge of the articulating surface, wherein the first edge is at a different elevation from the second edge, with elevation being defined with respect to a top surface of the intermediate implant.

An embodiment of the invention comprises a kit comprising a tibial implant, a talar implant and a plurality of intermediate implants, wherein the intermediate implants attach to the tibial implant and have respective articulating surfaces that articulate with respect to the talar implant, wherein at least one of the intermediate implants has a different elevational dimension of the first end point from another of the intermediate implants or has a different elevational dimension of the second end point from another of the intermediate implants.

An embodiment of the invention comprises a tibial implant, a talar implant and an intermediate implant, wherein the intermediate implant attaches to the tibial implant and is capable of articulating with respect to the talar implant, wherein one of the tibial implant and the intermediate implant comprises a pocket and the other of the tibial implant and the intermediate implant comprises a latch, the latch and the pocket engaging with each other upon assembly, wherein the intermediate implant comprises an intermediate implant recess on an anterior edge thereof, and wherein when viewed along an anterior-posterior direction, the intermediate implant recess at least partially aligns with the pocket and the latch.

An embodiment of the invention comprises a tibial implant, a talar implant and an intermediate implant, wherein the intermediate implant attaches to the tibial implant and is capable of articulating with respect to the talar implant, wherein the tibial implant has a tibia-facing surface and a lower surface opposed to the tibia-facing surface, wherein the lower surface has a cutout region extending in from an exterior perimeter of the tibial implant, the cutout region defined by a cutout perimeter shape that demarcates the cutout region from a remainder of the lower surface of the tibial implant, wherein the cutout perimeter has a tibial dovetail configuration, wherein the tibial dovetail configuration extends along two sides and at least a portion of a remainder of the cutout perimeter, and wherein the intermediate implant comprises an intermediate implant dovetail having an intermediate implant dovetail configuration that is complementary to the tibial dovetail configuration.

An embodiment of the invention comprises a tibial implant, a talar implant, and an intermediate implant fitting between the tibial implant and the talar implant, wherein the tibial implant has a tibia-facing surface and a lower surface opposed to the tibia-facing surface, wherein the lower surface has a cutout region defined by a perimeter shape demarcating the cutout region and a non-cutout region, the perimeter shape meeting an anterior edge of the tibial implant, wherein the tibia-facing surface has at least one tibial peg protruding therefrom and attached to the tibia-facing surface at an attachment region, wherein, as viewed along a direction perpendicular to the tibia-facing surface, the attachment region partially overlies the non-cutout region and partially overlies the cutout region.

An embodiment of the invention comprises a tibial implant comprising a tibia-facing surface and an opposed surface, wherein the tibia-facing side comprises a flat surface; and two pegs protruding from the tibia-facing surface; and a fin protruding from the tibia-facing surface, wherein, in a cross-section taken perpendicular to its long direction, the fin has a wide direction and a narrow direction, the wide direction being longer than the narrow direction, and the wide direction being generally perpendicular to a direction of advancement of the tibial implant, wherein the fin has a wedge-shaped end away from the tibia-facing surface that is, wherein the pegs are at least partially axisymmetric having respective axes of symmetry, wherein an anterior edge of the tibial implant is an edge having a cutout therein and a posterior direction is a direction that is opposed to the anterior edge, and the fin is more posterior than the pegs, wherein the fin has a fin centerline and the pegs have respective peg axes of symmetry, and the peg axes of symmetry and the fin centerline are all substantially parallel to each other.

In an embodiment of the invention, the tibial implant may have an outer perimeter such that, upon proceeding counterclockwise as viewed from above, the perimeter comprises a first straight edge; the first straight edge being followed by a first convex corner that meets and is tangent to the first straight edge; the first convex corner being followed by a second straight edge or a shallow arc that meets and is tangent to the first convex corner, wherein an angle of the first convex corner is greater than 90 degrees but less than 180 degrees; the second straight edge or the shallow arc being followed by a second convex corner that meets and is tangent to the second straight edge or the shallow arc; the second convex corner being followed by a first concave curve, wherein the second convex corner transitions to the first concave curve at a first inflection point, wherein there is a tangent line that is parallel to the first straight edge and is tangent to second convex corner at a tangency point that is farther from first straight edge than is the first inflection point, wherein the first concave curve continues on to cross the tangent line so as to become farther from the first straight edge than is the tangent line; wherein the first concave curve is followed by a convex curve that proceeds from the first concave curve and returns to the first straight edge to form a complete perimeter of the tibial plate.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

Figure 1A:
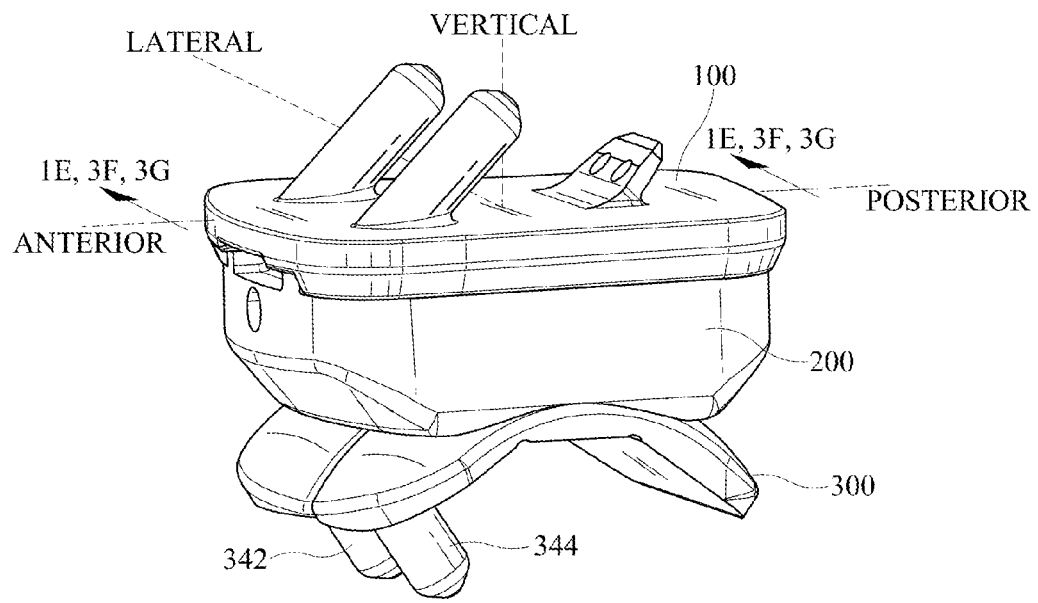
FIG. 1A shows a three-dimensional view of an embodiment of the invention, in its assembled configuration.
Figure 1B:
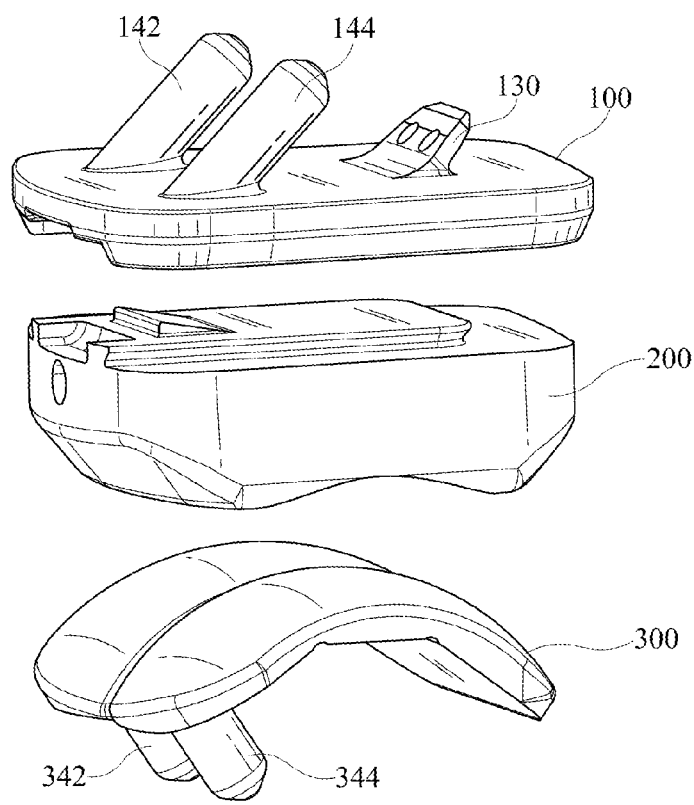
FIG. 1B shows the same three-dimensional view of an embodiment of the invention, in an exploded configuration.
Figure 1C:
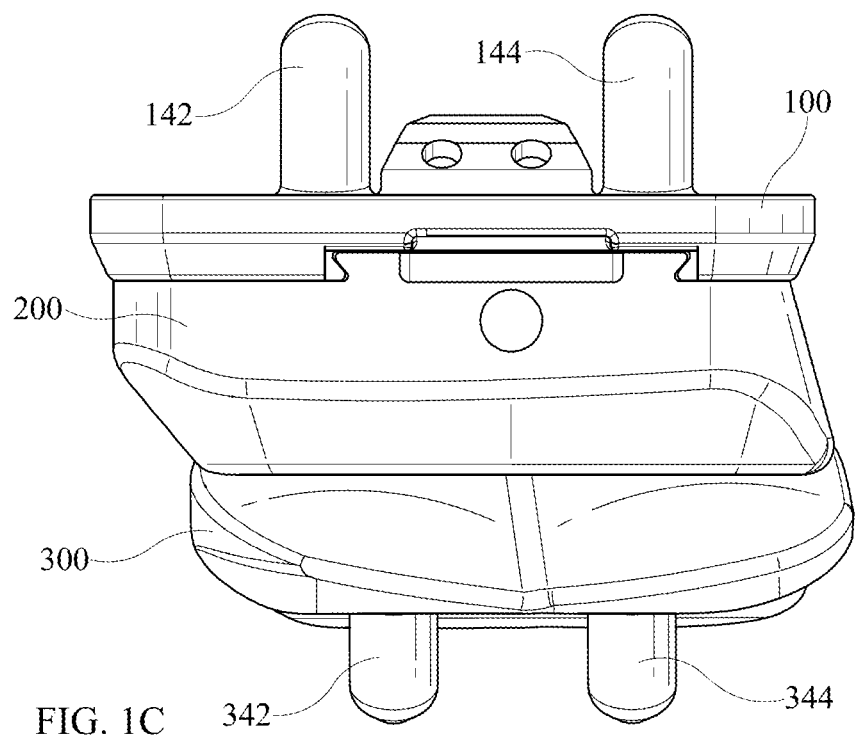
FIG. 1C shows a front view of an embodiment of the invention.
Figure 1D:
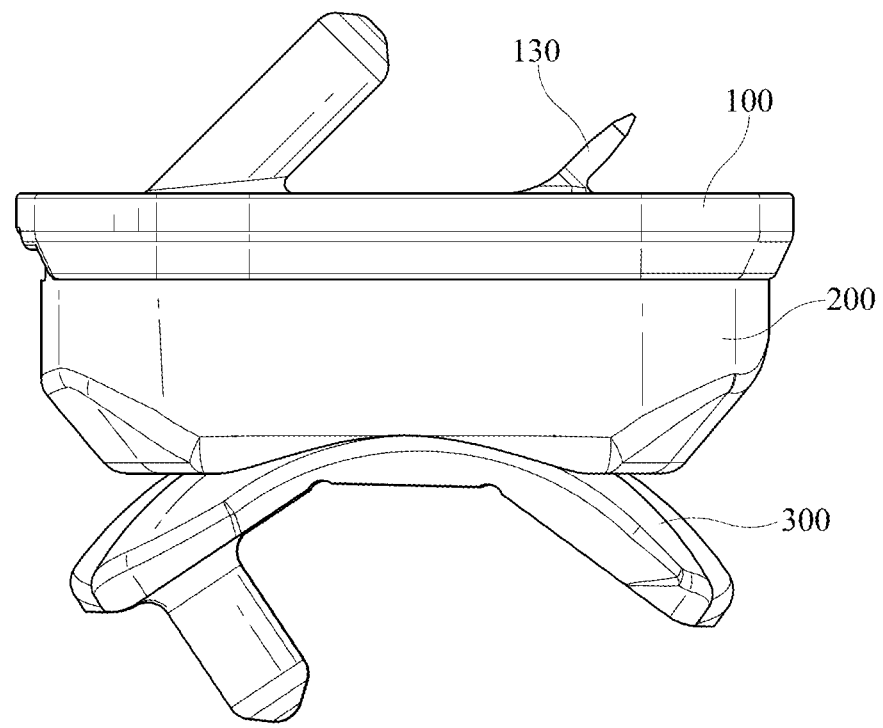
FIG. 1D shows a side view of an embodiment of the invention.
Figure 1E:
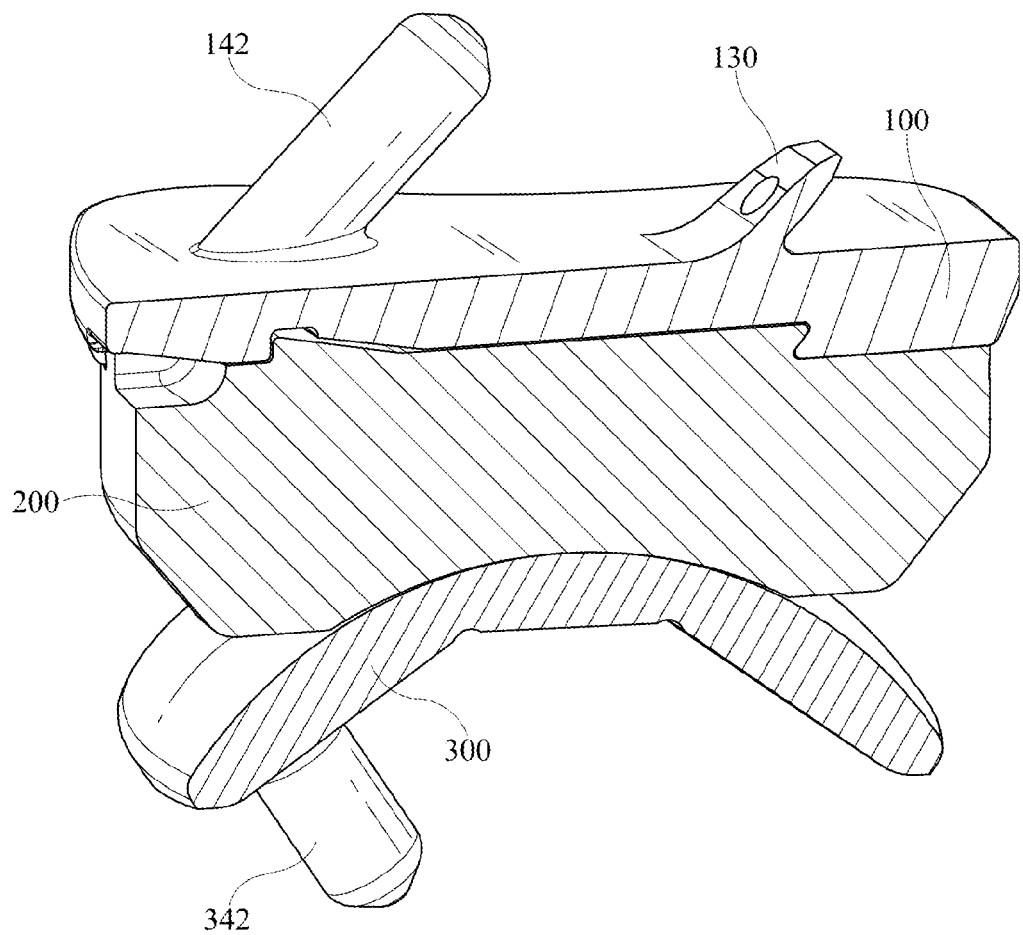
FIG. 1E shows a three-dimensional view of a section of an embodiment of the invention, as defined in FIG. 1A.

The following description discloses embodiments of a total ankle replacement device.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

The method and system disclosed herein are presented in terms of a device for use in the ankle. It will be obvious to those of ordinary skill in the art that this same configuration and method can be utilized in a variety of applications that require a prosthesis that provides motion. Nothing in this disclosure should be interpreted, unless specifically stated as such, to limit the application of any method or system disclosed herein to the ankle.

Referring now to FIGS. 1A through 1E, an embodiment of the invention comprises an assembly that comprises a tibial implant 100, a talar implant 300, and an intermediate implant 200 that can fit between the tibial implant 100 and the talar implant 300. The tibial implant 100 may be suitable for implantation into or onto a prepared end of a tibia. The talar implant 300 may be suitable for implantation into or onto a prepared surface of a talus. The intermediate implant 200 may attach to tibial implant 100 and may articulate with respect to talar implant 300.

Referring now to FIGS. 2A through 2K, there is shown a tibial implant 100. Tibial implant 100 may comprise an anterior edge 101A and a posterior edge 101P, although it is understood that this nomenclature is only for sake of description. The tibial implant 100 may comprise a tibia-facing surface 102 and a lower surface 104 that is generally opposed to the tibia-facing surface 102. The tibia-facing surface 102 may comprise a portion that is generally flat.

The lower surface 104 may comprise an outer surface 106, which may be flat, and an inner surface 108, which may be part of a cutout region and which may also may be flat. The cutout region defines a boundary with, as shown, first, second, and third internal boundary sides, 117, 119, and 121, respectively. It is not actually necessary that both the outer surface 106 and the inner surface 108 be flat, as other shapes are also possible in each case. The inner surface 108 of tibial implant 100 may have a centerline 109 generally along the anterior-posterior direction. Centerline 109 may be a line of symmetry of inner surface 108, which would be halfway between first boundary side 117 and second boundary side 119.

The boundary between outer surface 106 and inner surface 108 may comprise first and second dovetails 122 and 124, which may be straight and parallel to each other. More generally, in that location there may be any geometry that allows a sliding capture of a complementary feature of intermediate implant 200. Connecting between first dovetail 122 and second dovetail 124 may be yet another segment of the boundary between outer surface 106 and inner surface 108. As illustrated, this segment may comprise a third dovetail 126, which may occupy at least a portion of a remainder of the cutout perimeter other than first dovetail 122 and second dovetail 124. Third dovetail 126 may be geometrically identical to first and second dovetails 122, 124, although it does not have to be. First dovetail 122 and second dovetail 124 may be generally straight and may be parallel to each other. Third dovetail 126 may also be straight and may be perpendicular to first dovetail 122 or second dovetail 124, although this is not essential. There may be a rounded corner between the first dovetail 122 and third dovetail 126, and similarly another rounded corner between second dovetail 124 and third dovetail 126. These rounded corners may comprise the same dovetail shape as on the first second and third dovetails 122, 124, 126. Third dovetail 126 may be complementary to a corresponding feature of intermediate implant 200. At the anterior edge 101A of tibial implant 100, there may be provided an entrance region 111 to dovetails 122, 124 such that the entrance region 111 is wider in the medial-lateral direction than the space between dovetails 122, 124. Entrance region 111 may be tapered or otherwise shaped so as to guide intermediate implant 200 into its desired position within side dovetails 122, 124.

Extending from the tibia-facing surface 102 may be a plurality of projections. The projections may comprise a somewhat planar fin 130. It is possible that fin 130 may have one or more through-holes 132 therethrough. In cross-section taken perpendicular to its overall length direction, fin 130 may have two long sides 134, 136 and two short sides 138, 139. The two long sides 134, 136 may be part of flat surfaces that may be parallel or almost parallel to each other or may form a slight taper. Fin 130 may be sharp or wedge-shaped at its end away from tibia-facing surface 102 of tibial implant 100. The projections may also comprise one or more (two shown) tibial pegs 142, 144 that may be at least somewhat cylindrical. The joints where pegs 142, 144 join tibia-facing surface 102 may be located both on a common line that is perpendicular to a direction of the dovetails 122, 124. Tibial pegs 142, 144 preferably may be longer than fin 130. Tibial pegs 142, 144 preferably are located at a distance away from the centerline 109, and as such are inserted into the cancellous bone in the epiphysis. It is believed, although it is not wished to be limited to this explanation, that the use of a fin 130 may be helpful (compared to a peg, for example) in securing anchorage of tibial implant 100 into the bone of the distal portion of the tibia. The distal portion of the tibia is a region where the bone can be relatively soft, and the fin 130 has greater surface area than a peg would have, thereby securing its position more effectively. Also, the fin 130 may be self-cutting into the bone, without requiring preparation such as the pre-drilling of a hole. All of this may allow placement of fin 130 in a position fairly far distal in the tibia, which may be helpful in anchoring to the tibia particularly in preventing the tibial implant 100 from separating from the tibia during various possible scenarios of motion by the patient. Additionally, the absence of need for hole preparation in the less-accessible distal region of the tibia would be a convenience for the surgeon.

At least some of the projections may have a respective defined lengthwise direction. For a projection such as tibial pegs 142, 144 that is at least partly cylindrical or axisymmetric, the lengthwise direction may be the axis of the cylinder or the axis of axisymmetry of the tibial peg 142, 144. Tibial pegs 142, 144 may have a portion of a sphere 148A at the tip of the peg, which may be followed by a portion of a cone 148B, which may be followed by surface 148C formed by a circular arc in revolution around the longitudinal axis of the tibial peg, which may be followed by a cylindrical surface 148D. It is believed, although it is not wished to be limited to this explanation, that such a shape of the tip of the tibial peg 142, 144 may be helpful in guiding the pegs 142, 144 into the corresponding hole prepared in the bone, which may involve a close fit between the peg 142, 144 and the prepared bone. For a fin 130, the lengthwise direction may be an axis that is midway between respective opposed parallel exterior surfaces of the fin. As illustrated, the tibial implant 100 may have a midpoint that is halfway between the anterior-most extent of the tibial implant 100 and the posterior-most extent of tibial implant 100, and fin 130 may be entirely located posteriorly of the midpoint.

The defined lengthwise direction of any of the projections may be inclined at an angle gamma with respect to the generally flat portion of tibia-facing surface 102 of tibial implant 100. The angle may be such that the angle gamma faces toward the posterior of tibial implant 100 and has an angular measure of between 0 and 90 degrees, more particularly between 20 and 70 degrees. As illustrated, the angle gamma is 45 degrees. Gamma is illustrated in FIG. 2B as being identical for tibial pegs 142, 144 and for fin 130, but it is possible that the angle designated as gamma for tibial pegs 142, 144 could have a different value from the angle designated as gamma for fin 130. The inequality of angle could be in either direction, in terms of which angle is greater than which other angle.

The respective lengthwise directions of at least some of the projections (tibial pegs 142, 144 and fin 130) may be parallel to each other. The directional axis of fin 130 may be parallel to the respective axis of one or more tibial pegs 142, 144. Alternatively, the axis of a tibial peg 142, 144 may be parallel to a straight-line segment of a surface of the fin 130. Pegs 142, 144 and fin 130 may be spaced so as to occupy more than one position along the anterior-posterior direction of the tibial implant 100, i.e. pegs 142, 144 and fin 130 can be positioned so as to not all lie in a line running medial-lateral (not all in the same coronal plane). It is possible that pegs 142, 144 may occupy the same position as each other along the anterior-posterior direction of tibial implant 100, and fin 130 may occupy a different position (i.e. they can lie in the same coronal plane). Fin 130 may be more posterior than pegs 142, 144.

Tibial implant 100 may further comprise a pocket 160, which may be recessed with respect to inner surface 108. As described elsewhere herein, pocket 160 may be dimensioned so as to cooperate with a feature of intermediate implant 200 to latch intermediate implant 200 to tibial implant 100. The pocket 160 of tibial implant 100 may have side edges that are parallel or at least approximately parallel to the first and second dovetails 122, 124 of tibial implant 100, or may have any other suitable geometry. Pocket 160 may be located either approximately or exactly midway between the first and second dovetails 122, 124 of tibial implant 100.

It is further possible that tibial implant 100 may comprise a tibial implant recess 170, which may be located at the anterior edge 101A of tibial implant 100. Tibial implant recess 170 may have a lateral dimension that is substantially the same as the lateral dimension of pocket 160 or of latch 260 (described hereinafter) of intermediate implant 200. Tibial implant recess 170 may substantially align with pocket 160 along the direction of side dovetails 122, 124. Tibial implant recess 170 may be located either approximately or exactly midway between the side dovetails 122, 124 of tibial implant 100.

Figure 2A:
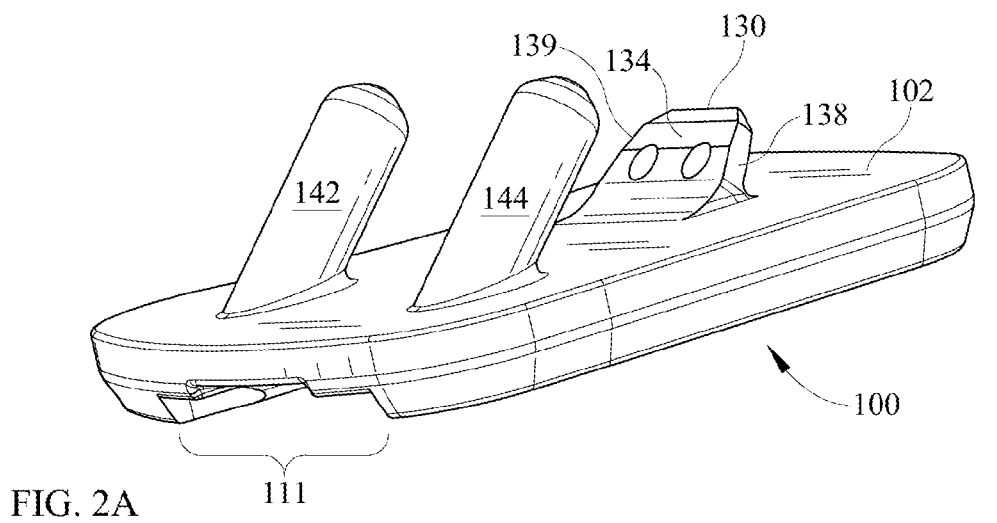
FIG. 2A shows a three-dimensional view of the tibial implant.
Figure 2B:
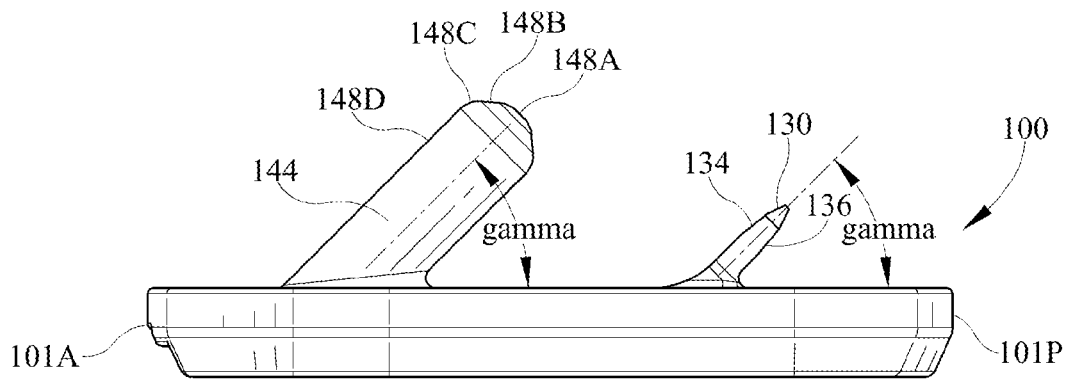
FIG. 2B is a side view of the tibial implant.
Figure 2C:
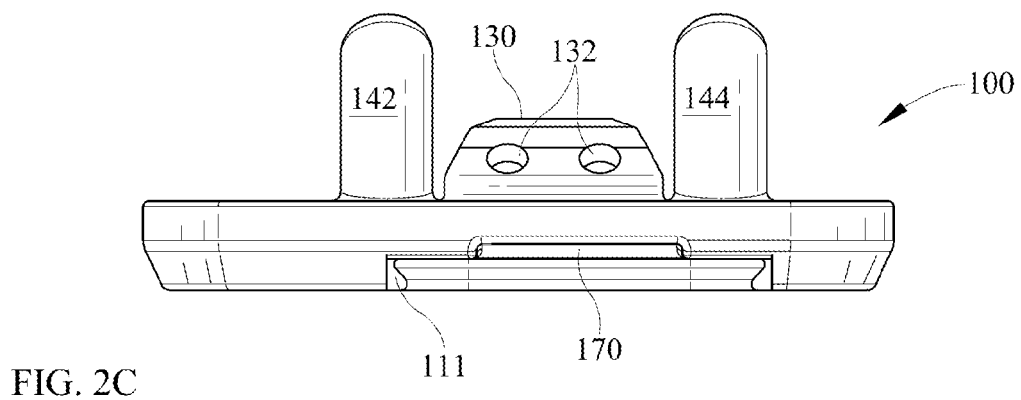
FIG. 2C is a front view of the tibial implant.
Figure 2D:
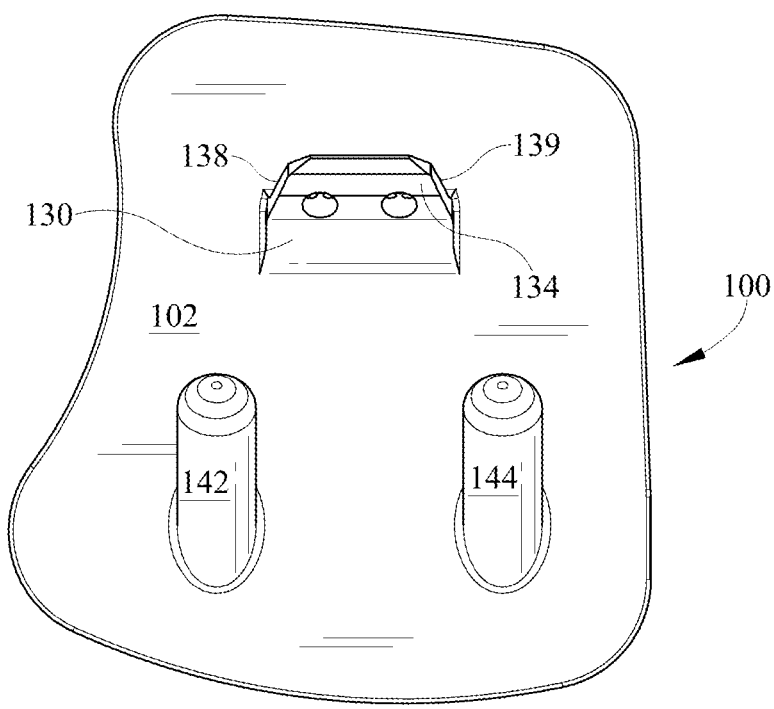
FIG. 2D is a top view of the tibial implant.
Figure 2E:
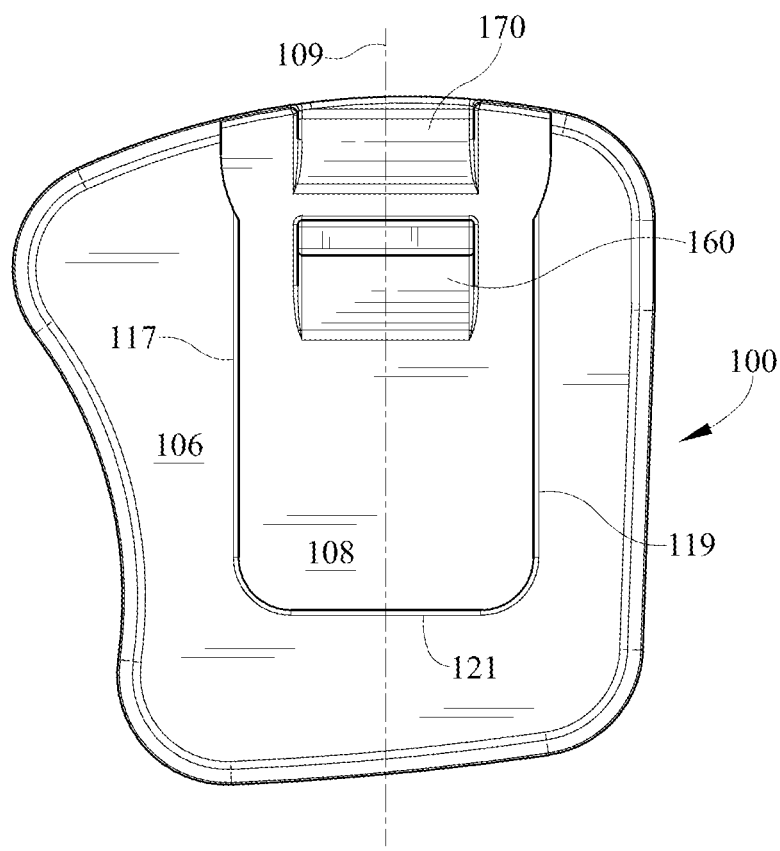
FIG. 2E is a bottom view of the tibial implant.
Figure 2F:
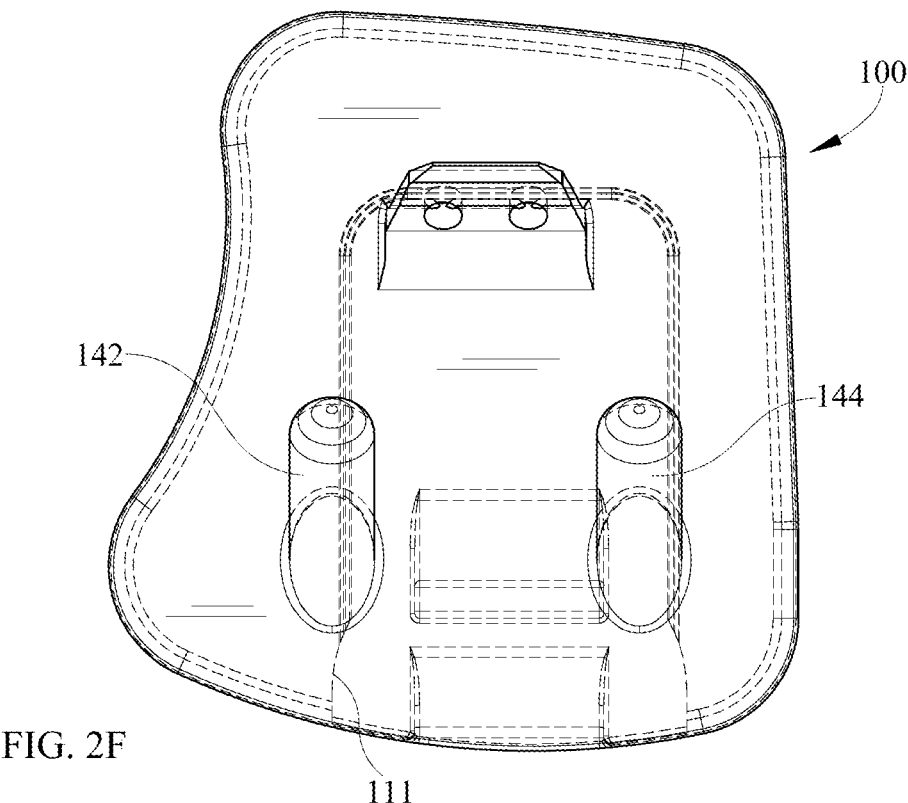
FIG. 2F is a top view of the tibial implant as if it were transparent.
Figure 2G:
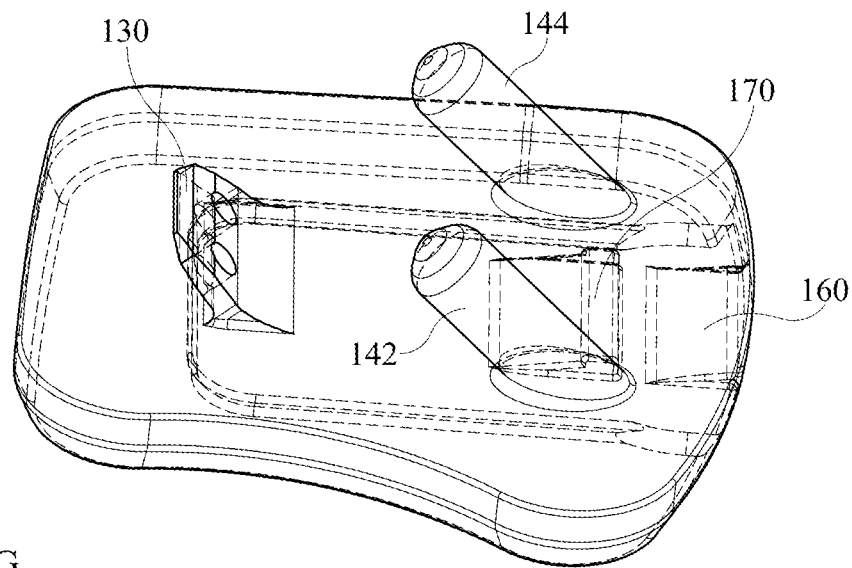
FIG. 2G is a three-dimensional view of the tibial implant as if it were transparent.

Referring now to FIG. 2F, there is shown a top view of tibial implant 100 with the tibial implant 100 being a transparent wireframe so that features on the underside of tibial implant 100, such as dovetails 122, 124 and 126 and pocket 160 can be seen in relation to features on the upper side of tibial implant 100 such as pegs 142, 144 and fin 130. Similarly, FIG. 2G, which is a three-dimensional perspective view, shows tibial implant 100 as a transparent wireframe so as to show the relative placement of certain features on the upper side and the underside. There may be certain relations between the placement of features on the upper side and the placement of features on the underside of tibial implant 100. Such relative placement can serve to connect protruding load-bearing features such as pegs 142, 144 and fin 130 to portions of tibial implant 100 that are structurally thick and strong. In other instances, such placement may overlap thicker stronger portions of tibial implant 100 with regions that are thinner and structurally weaker, and may thereby help to reinforce regions that are thinner and structurally weaker. As illustrated, the connection of fin 130 to tibial implant 100 is entirely within the region of dovetails 122, 124 and 126, i.e., the connection of fin 130 to tibial implant 100 is opposite the inner surface 108. However, it would also have been possible that the connection of fin 130 could partially overlie the inner surface 108 within dovetails 122, 124 and 126 and could partly overlie the thicker portion of tibial implant 100, outer surface 106, that does not have dovetails 122, 124 and 126 cut out of it. Tibial pegs 142, 144 may, as illustrated, partially overlie the inner surface 108 within dovetails 122, 124 and 126 and partially overlie the thicker portion of tibial implant 100, outer surface 106, that does not have dovetails 122, 124 and 126 cut out of it. This could structurally reinforce the thinner portion (inner surface 108) of tibial implant 100.

Figure 2H:
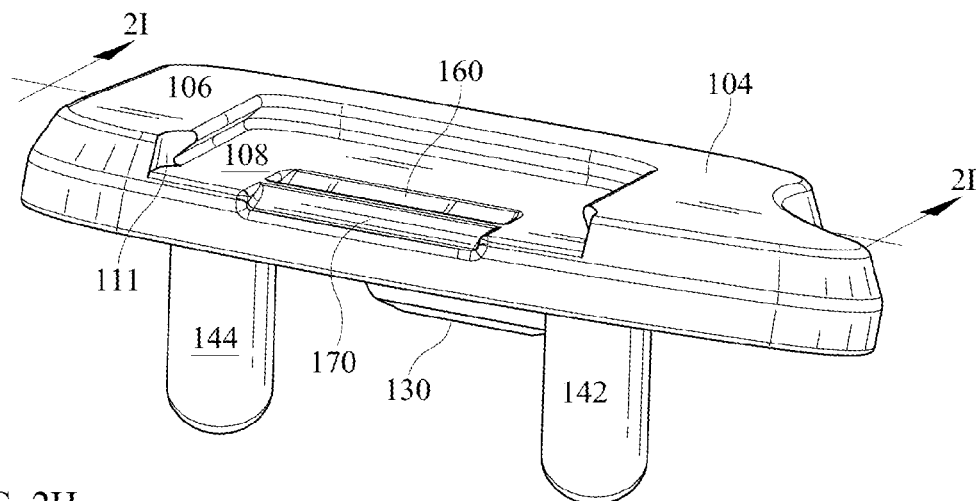
FIG. 2H shows a three-dimensional view of the tibial implant, upside-down compared to its orientation in FIG. 2A.
Figure 2I:
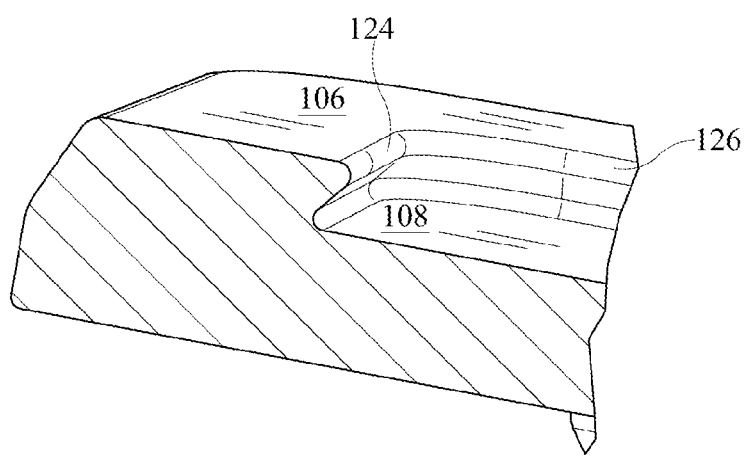
FIG. 2I is a three-dimensional view of a section of the tibial implant, as defined in FIG. 2H.
Figure 2J:
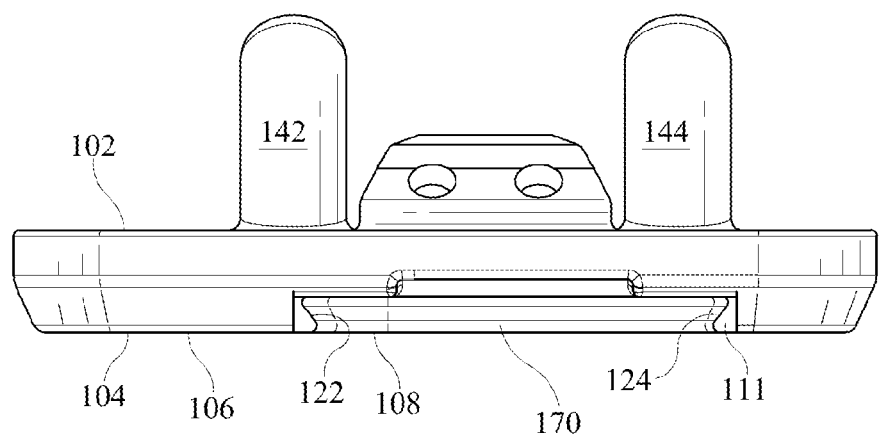
FIG. 2J is a frontal view of the tibial implant similar to FIG. 2C, but with sectioning removing the posterior portion of the tibial implant, so as to make the dovetail more visible.

Referring now to FIGS. 2H and 2I, there is shown a three-dimensional view of the tibial implant 100, upside-down compared to its orientation in FIG. 2A. It can be seen that pocket 160 is recessed from inner surface 108. Entrance region 111 also is visible, as is tibial implant recess 170. FIG. 2J shows the edges of first and second dovetails 122, 124 visible in this anterior view.

Figure 2K:
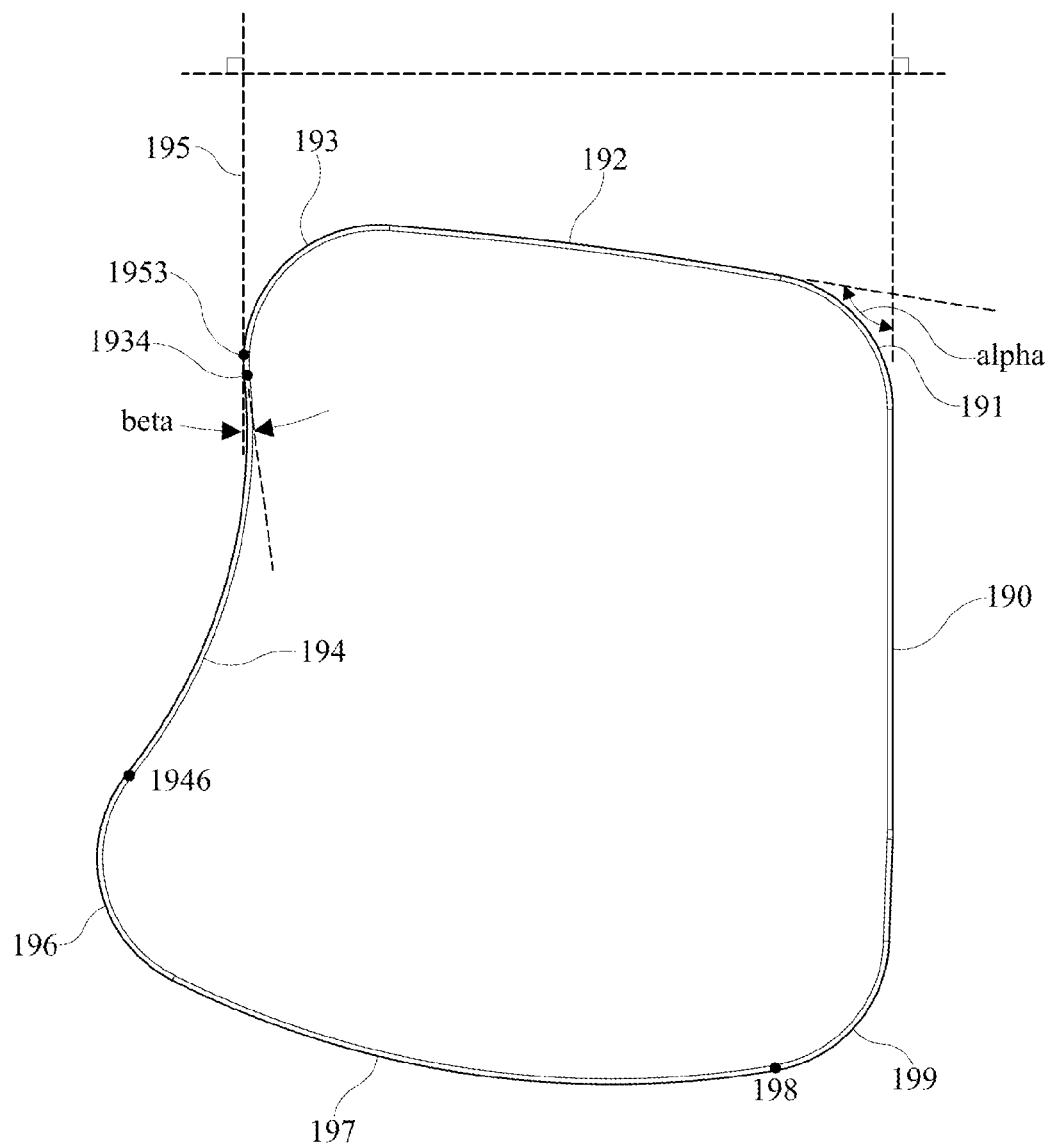
FIG. 2K is a top view of the tibial implant similar to FIG. 2D, but with specific reference to the external perimeter of the tibial implant.

Referring now to FIG. 2K, the tibia-facing surface 102 may have an external shape that is chosen so as to match closely with the external shape of the prepared lower end of the tibia, when the tibia end is prepared as described elsewhere herein. The tibia, as with bones generally, comprises an outer region of cortical bone that is relatively strong, and an inner region of cancellous bone that is more porous and less strong. The close matching of the external shape of the tibial implant to the outside perimeter shape of the prepared end of the lower tibia is believed to give good mechanical contact and load transfer between the tibial implant and the cortical region of the bone of the tibia. It is believed, although it is not wished to be limited to this explanation, that this close matching of shapes may decrease the likelihood of problems with subsidence of the tibial implant into the tibia.

The tibial implant 100 may, first of all, have a perimeter that has a certain external perimeter shape, as is best illustrated in FIGS. 2D and 2K. FIG. 2K is a top view of the outside perimeter of tibial implant 100. The perimeter may, first of all have a first straight edge 190. The side dovetails 122, 124 of tibial implant 100 may be close to being parallel to straight external edge 190 of tibial implant 100, although as illustrated they are not exactly parallel.

The tibial implant 100 may have an outer perimeter that can be described as follows, while commencing at a location on the lateral edge of the implant 100 at a posterior location and proceeding counterclockwise as viewed from above. From this vantage point, the perimeter may comprise: a first straight edge 190, which may be considered a vertical reference for purpose of illustration; followed by a first convex corner 191 that meets and is tangent to the first straight edge 190; followed by a second straight edge or shallow arc 192 that meets and is tangent to the first convex corner 191, wherein an angle alpha of the first convex corner 191 is greater than 90 degrees but less than 180 degrees; followed by a second convex corner 193 that meets and is tangent to the second straight edge or shallow arc 192; followed by a first concave curve 194, wherein the second convex corner 193 transitions to the first concave curve 194 at a first inflection point 1934. It may be considered that there is a tangent line 195 that is parallel to first straight edge 190 and is tangent to second convex corner 193 at a tangency point 1953, wherein the tangency point 1953 is farther from first straight edge 190 than is first inflection point 1934. The second convex corner 193 and the first concave curve 194 have a common tangent line at the first inflection point 1934, wherein the tangent line to the curve at the inflection point 1934 forms an angle beta with respect to tangent line 195, with beta being greater than zero so that the perimeter shape is re-entrant with respect to the first straight edge 190. First concave curve 194 may then continue until it again crosses tangent line 195 so that the perimeter crosses tangent line 195 to become farther from first straight edge 190 than is tangent line 195. Continuing on from first concave curve 194 may be an arbitrary convex curve that returns to first straight edge 190 to form a complete perimeter of tibial plate 100. In an anatomical sense, features such as first concave curve 194 may be located on the lateral side of the tibial implant 100, as distinguished from the medial side of the tibial implant 100. Correspondingly, first straight edge 190 may be located on the medial side of tibial implant 100.

As illustrated, first concave curve 194 may be followed by a third convex corner 196, wherein the first concave curve 194 transitions to the third convex corner 196 at a second inflection point 1946; third convex corner 196 may be followed by a first convex curve 197, wherein the third convex corner 196 transitions to the first convex curve 197 at a common tangency point; followed by a fourth convex corner 199, wherein the first convex curve 197 transitions to the fourth convex corner 199 at a common tangency point 198; wherein the fourth convex corner 199 continues on and meets and is tangent to the first straight edge 190.

Referring now to FIGS. 3A-3E, there is shown intermediate implant 200. Intermediate implant 200 may comprise a top surface 202 that faces tibial implant 100. First of all, the intermediate implant 200 may have an external perimeter, when viewed from above, that is similar to the corresponding perimeter of tibial implant 100 which it touches. Intermediate implant 200 may have a top surface 202, which may be flat. There may be a projection 204 protruding from top surface 202. Projection 204 may have projection surface 206, which may be flat and may be parallel to top surface 202. Between top surface 202 and projection surface 206, intermediate implant 200 may have external dovetails suitable to engage corresponding dovetails 122, 124, 126 of tibial implant 100. There may be side dovetails 222 and 224, which may be parallel to each other. There may further be end dovetail 226. End dovetail 226 may be continuous with side dovetails 222, 224 through rounded corners. The rounded corners may also have dovetails, which may have the same cross-sectional shape as dovetails 222, 224, 226.

The intermediate implant 200 may have a latch 260, which may project beyond the surface 202 of intermediate implant 200. Latch 260 may serve to lock intermediate implant 200 relative to tibial implant 100. The latch 260 may be shaped generally complementary to the pocket 160 in the tibial implant 100. The intermediate implant 200 may be capable of deforming or flexing slightly during insertion of the intermediate implant 200 into the tibial implant 100, to allow the latch 260 to attain its final position. Alternatively, or in addition, the latch 260 itself may be capable of deforming or flexing slightly during insertion towards accomplishing a similar purpose. For example, latch 260 could comprise a living hinge.

It is further possible that intermediate implant 200 may comprise an intermediate implant recess 270, which may be located on the anterior edge of intermediate implant 200. Intermediate implant recess 270 may be located in a location similar to the location of recess 170 of tibial implant 100. Intermediate implant recess 270 may have a lateral dimension that is substantially the same as the lateral dimension of latch 260 of intermediate implant 200. Intermediate implant recess 270 may substantially align with latch 260 along the direction of side dovetails 122, 124. Tibial implant recess 170 may have an internal slope and latch 260 may have an external slope, and the tibial implant recess internal slope and the latch external slope may be equal to each other.

Figure 3A:
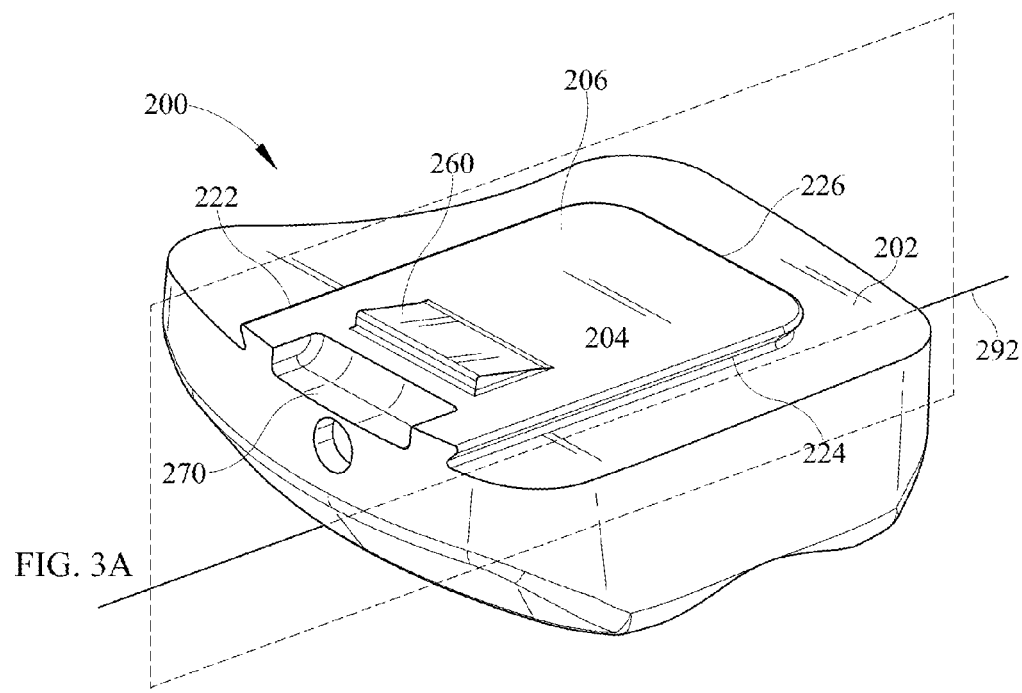
FIG. 3A is a three-dimensional view of an intermediate implant.
Figure 3B:
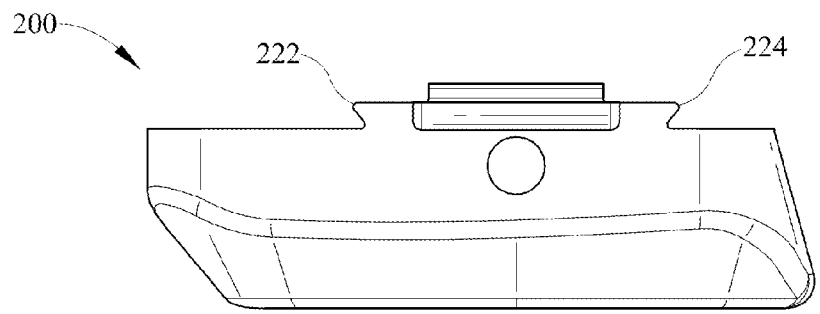
FIG. 3B is a front view of the intermediate implant of FIG. 3A.
Figure 3C:
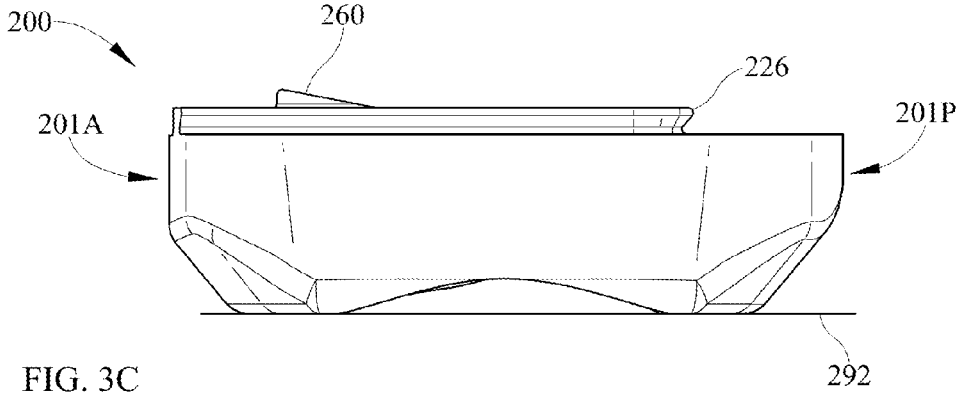
FIG. 3C a side view of the intermediate implant of FIG. 3A.
Figure 3D:
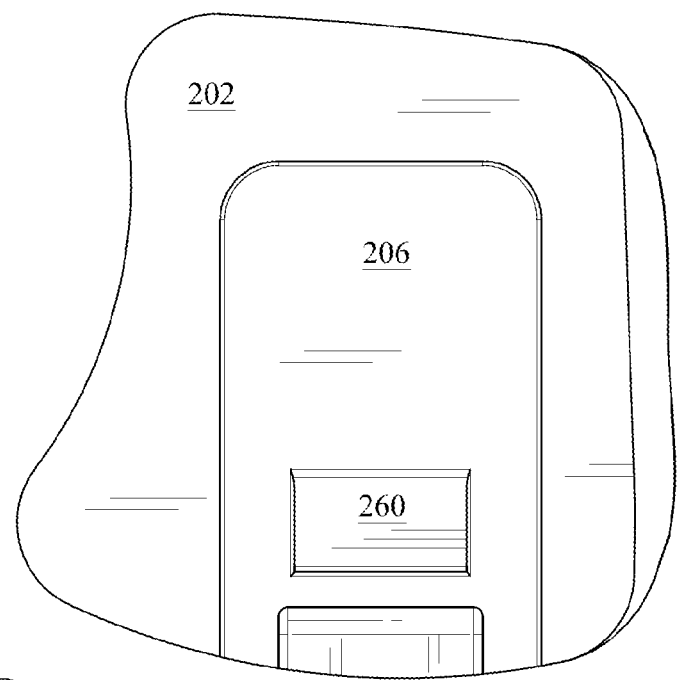
FIG. 3D is a top view of the intermediate implant of FIG. 3A.
Figure 3E:
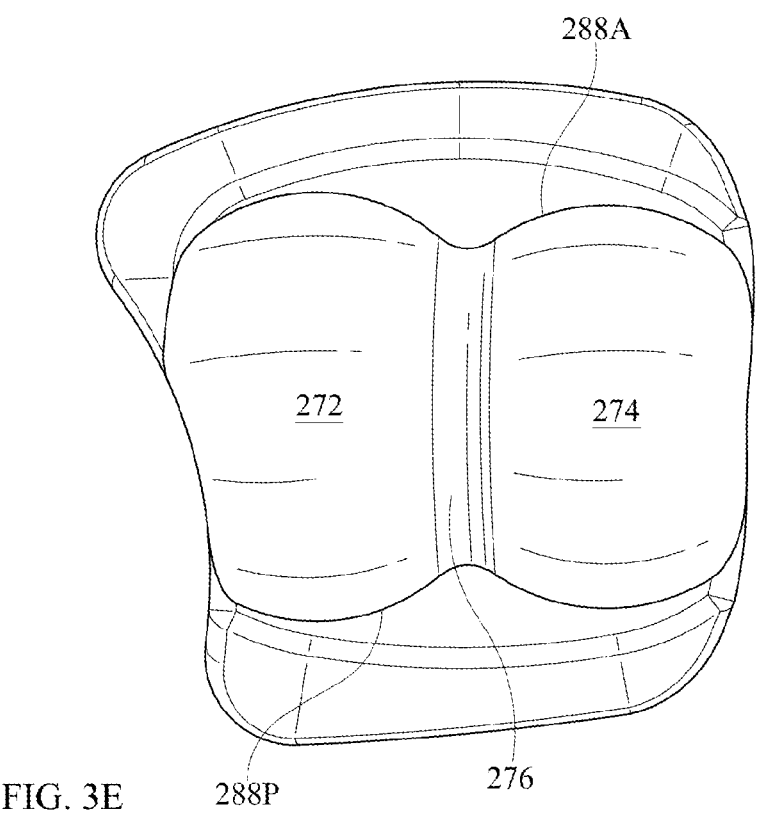
FIG. 3E is a bottom view of the intermediate implant of FIG. 3A.
Figure 5A:
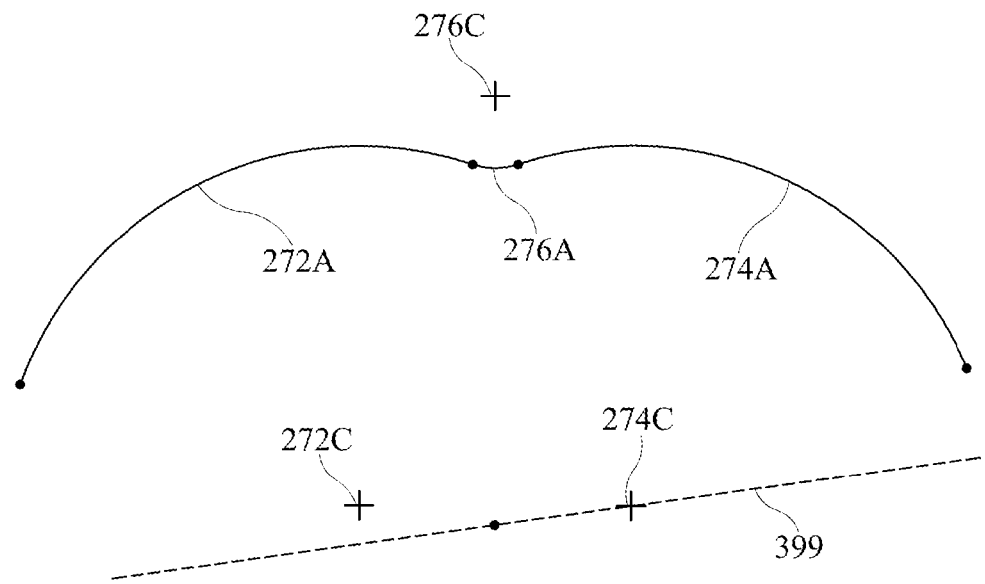
FIG. 5A is an illustration of the shape, in cross-section, of the bicondylar surface of the intermediate implant.
Figure 5B:
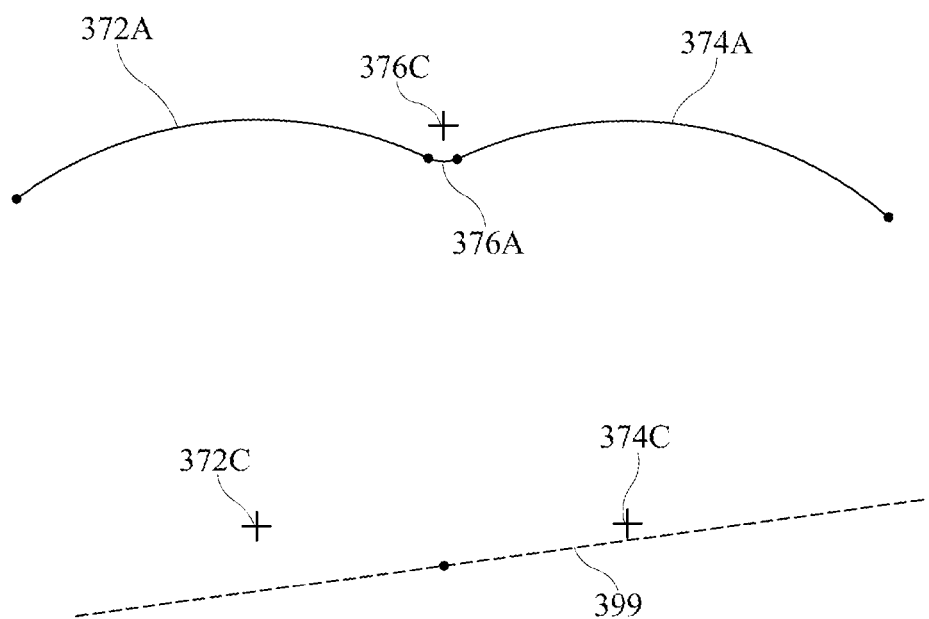
FIG. 5B is an illustration of the shape, in cross-section, of the bicondylar surface of the talar implant.

Opposite to tibia-facing top surface 202, intermediate implant 200 may have an opposed surface that is an articulating surface (FIG. 3E). The articulating surface may comprise, as illustrated, two condyles, although other shapes are also possible. The first condylar articulating surface 272 and the second condylar articulating surface 274, as illustrated, may both be concave. However, in the region where the two condylar articulating surfaces approach each other, there may be a transition surface 276, which may be convex. As illustrated here and elsewhere herein, first condylar surface 272, second condylar surface 274 and transition surface 276 may all be formed by respective circular arcs being revolved around an axis of revolution 399. Furthermore, as illustrated in FIGS. 5A and 5B, the circular arc for first condylar surface 272 and the circular arc for second condylar surface 274 may have identical radii of curvature, although this is not essential. As illustrated, the circular arc for first condylar surface 272 and the circular arc for second condylar surface 274 both have a radius of curvature of 0.820 inch. As illustrated, transition surface 276 has a radius of curvature of 0.100 inch in the opposite sense from surfaces 272, 274. Variations from all of these dimensions would be possible.

Figure 3F:
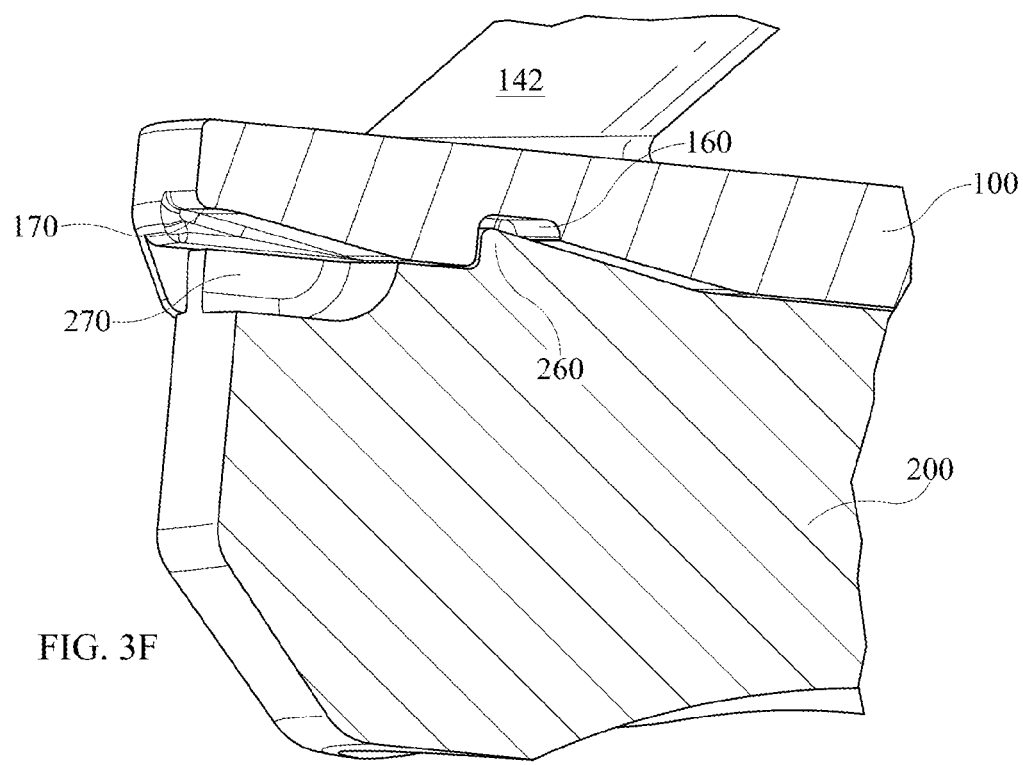
FIG. 3F is a three-dimensional sectional view of the tibial implant and the intermediate implant showing especially the recesses at the anterior of the tibial implant and the intermediate implant and the latch of the intermediate implant and the pocket of the tibial implant.
Figure 3G:
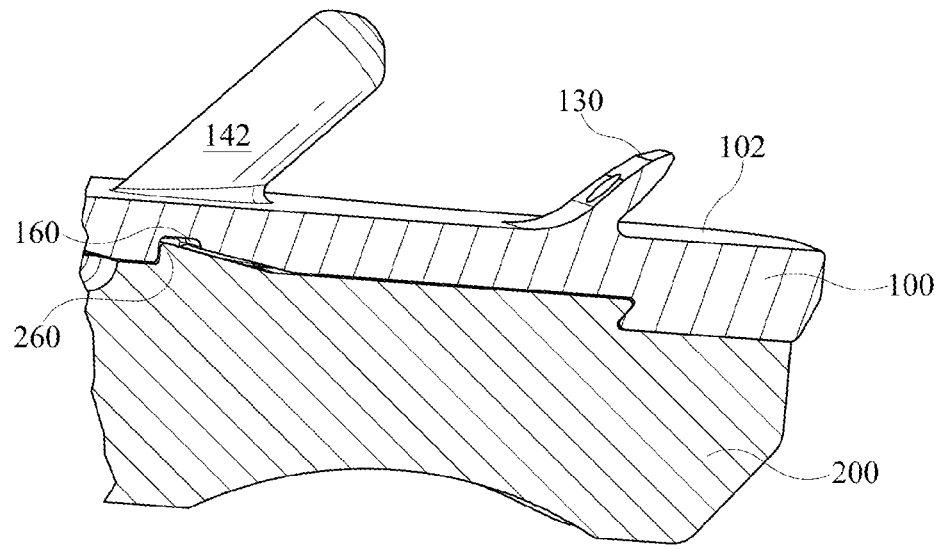
FIG. 3G is a three-dimensional sectional view of the tibial implant and the intermediate implant showing especially the latch of the intermediate implant and the cutout and the pocket of the tibial implant.

Referring now to FIGS. 3F-3G, there may exist certain geometric relationships that relate features of tibial implant 100 and features of intermediate implant 200. In regard to dovetail features, the respective sides of external dovetail 222, 224, 226 of intermediate implant 200 may have dimensions and shape that are complementary to those of the respective sides of internal dovetail 122, 124, 126. The relationship may be such as to allow the intermediate implant 200 to be slid into the tibial implant 100 and to be retained therein. The distance between the planes of outer surface 106 and inner surface 108 of tibial implant 100 may approximately equal or be slightly greater than the distance between the planes of top surface 202 and projection surface 206. Also, the end external dovetail 226 of intermediate implant 200 may be complementary to the end internal dovetail 126 of tibial implant 100. The relationship may be such as to further help retain intermediate implant 200 to tibial implant 100.

In regard to latching features, latch 260 of intermediate implant 200 may be complementary to pocket 160 in tibial implant 100 so as to allow latch 260 to reside within pocket 160 when intermediate implant 200 is assembled to tibial implant 100. Furthermore, the locations of latch 260 and pocket 160 may be such that this residing occurs when the side dovetails 222, 224 of intermediate implant 200 are engaged with the side dovetails 122, 124 of tibial implant 100, and when end dovetail 226 of intermediate implant 200 is engaged with the end dovetail 126 of tibial implant 100. The engagement of latch 260 with pocket 160 may coincide with engagement of end dovetail 226 with end dovetail 126. The distance between latch 260 and end dovetail 226 of intermediate implant 200 may be approximately equal to the distance between pocket 160 and end dovetail 126 of tibial implant 100. It can be noted that, in general, either one of the tibial implant 100 and the intermediate implant 200 may comprise a pocket and the other of the tibial implant 100 and the intermediate implant 200 may comprise a latch.

In regard to recesses at the anterior edges of tibial implant 100 and intermediate implant 200, tibial implant recess 170 may have a lateral dimension that is substantially the same as the lateral dimension of pocket 160 or of latch 260 of intermediate implant 200. Intermediate implant recess 270 may have a lateral dimension that is substantially the same as the lateral dimension of pocket 160 or of latch 260 of intermediate implant 200. Tibial implant recess 170 may substantially align with pocket 160 along the direction of side dovetails 122, 124. Intermediate implant recess 270 may substantially align with pocket 160 along the direction of side dovetails 122, 124. Intermediate implant recess 270 and tibial implant recess 170 may at least approximately align with each other to create a combined recess that may be suitable to receive and direct a surgical blade in the event that it is necessary to insert a surgical blade to cut off latch 260 for removal of intermediate implant 200 from tibial implant 100. It is possible that intermediate implant recess 270 alone could receive and direct a surgical blade in the event that it is necessary to insert a surgical blade to cut off latch 260, or tibial implant recess 170 alone could receive and direct a surgical blade in the event that it is necessary to insert a surgical blade to cut off latch 260.

Intermediate implant 200 may have an outer perimeter, at or near the end that faces tibial implant 100, that is generally similar in shape and dimension to the outer the outer perimeter of tibial implant 100 at or near the end of tibial implant 100 that faces intermediate implant 200.

Of course, it is also possible that pocket 160 of tibial implant 100 could instead be a protrusion and latch 260 of intermediate implant 200 could instead be a complementary void, or still other designs of latching or engaging features could be used.

Referring now to FIGS. 4A-4E, there is illustrated a talar implant 300. Anterior edge 301A and posterior edge 301P are illustrated, although this is only for descriptive purposes. Talar implant 300 may comprise a talar-facing surface 302 and an articulating surface that may be generally opposed to the talar-facing surface 302. Talar-facing surface may comprise three generally planar surfaces. The three planar surfaces may be anterior talar planar surface 306, central talar planar surface 307 and posterior talar planar surface 308. (It is not essential that any of these talar planar surfaces be planar.) The three generally planar surfaces 306, 307, 308 may appear, in cross-section when viewed from a lateral direction, as straight-line segments. Between adjacent planar surfaces 306, 307, 308 may be machining recesses or fillets 309A, 309B.

Figure 4A:
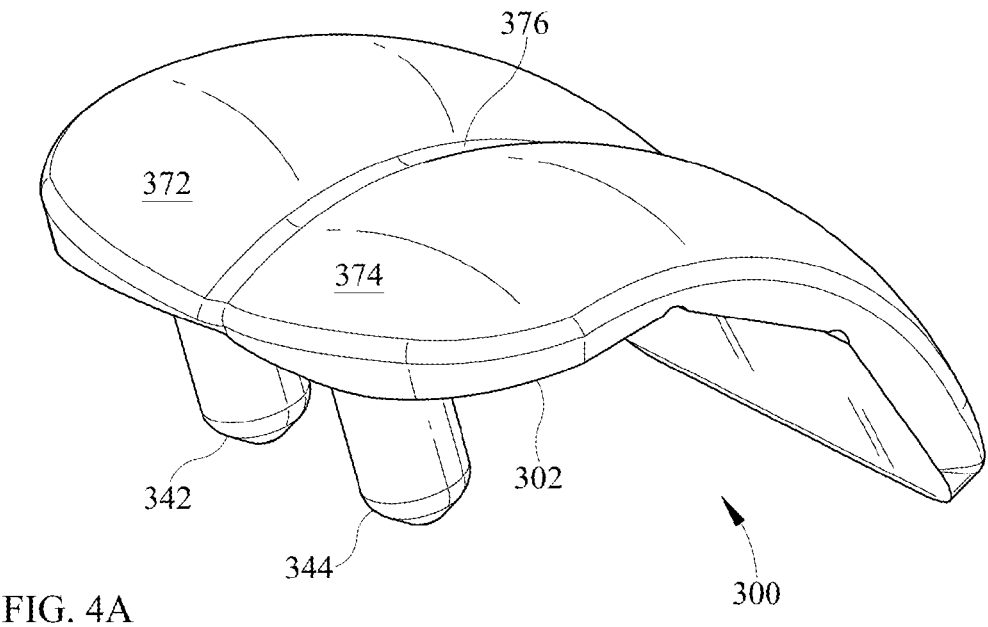
FIG. 4A is a three-dimensional view of a talar implant, somewhat from above.
Figure 4B:
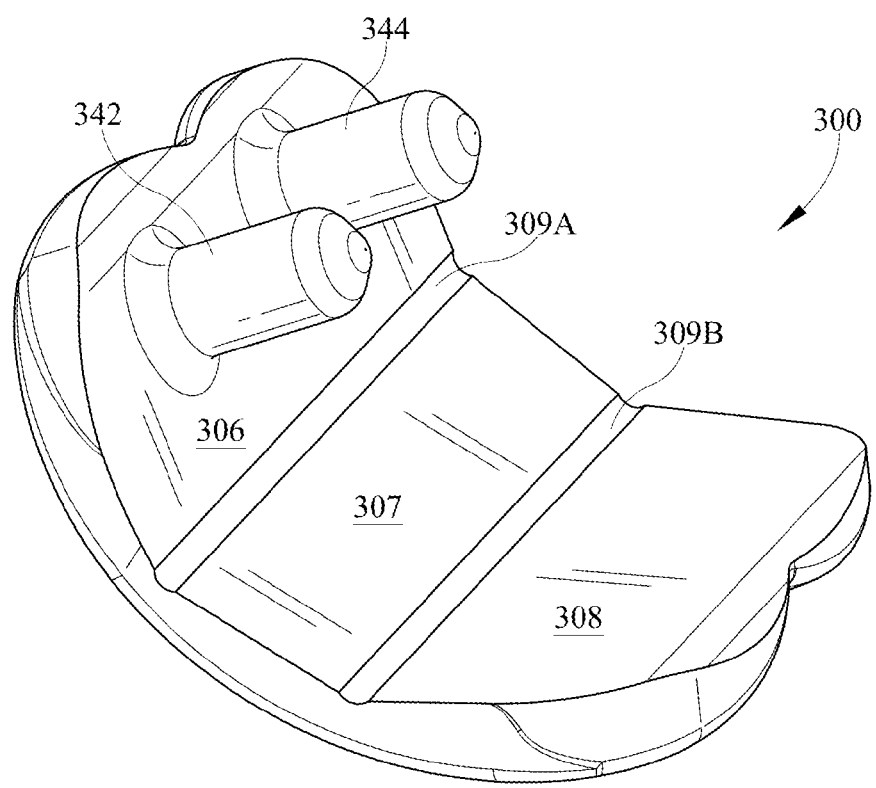
FIG. 4B is a three-dimensional view of the talar implant of FIG. 4A, somewhat from below.
Figure 4C:
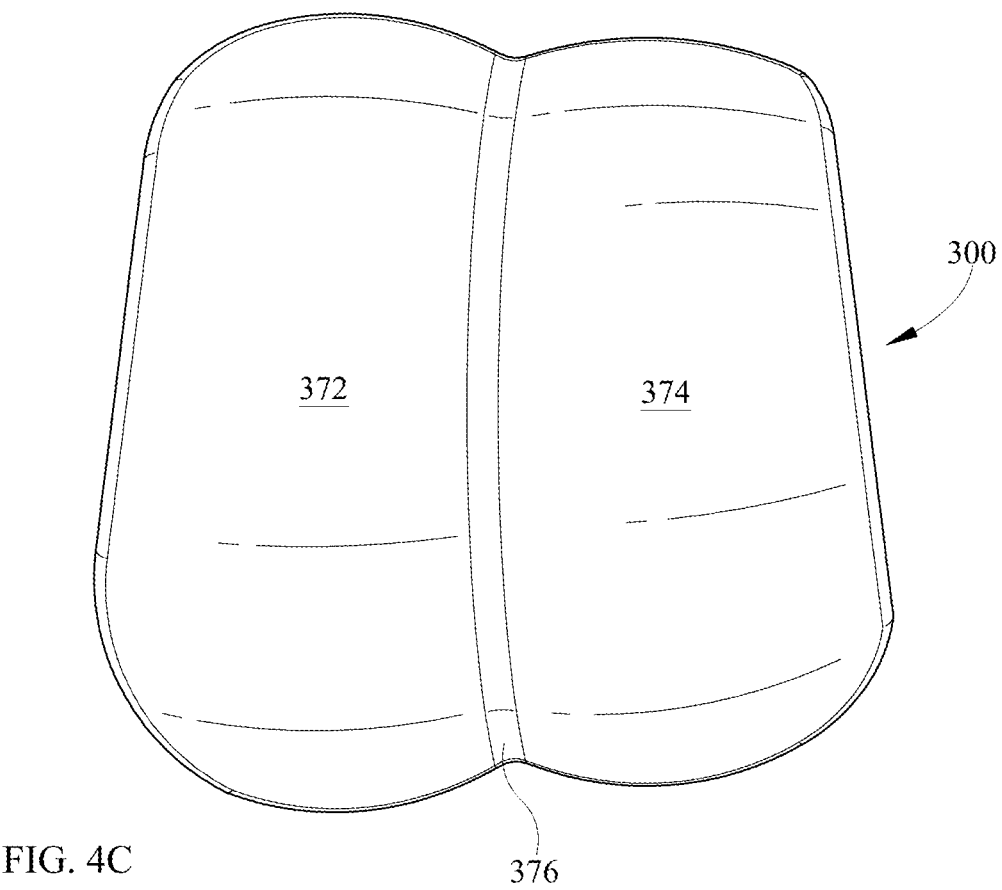
FIG. 4C is a top view of the talar implant of FIG. 4A.
Figure 4D:
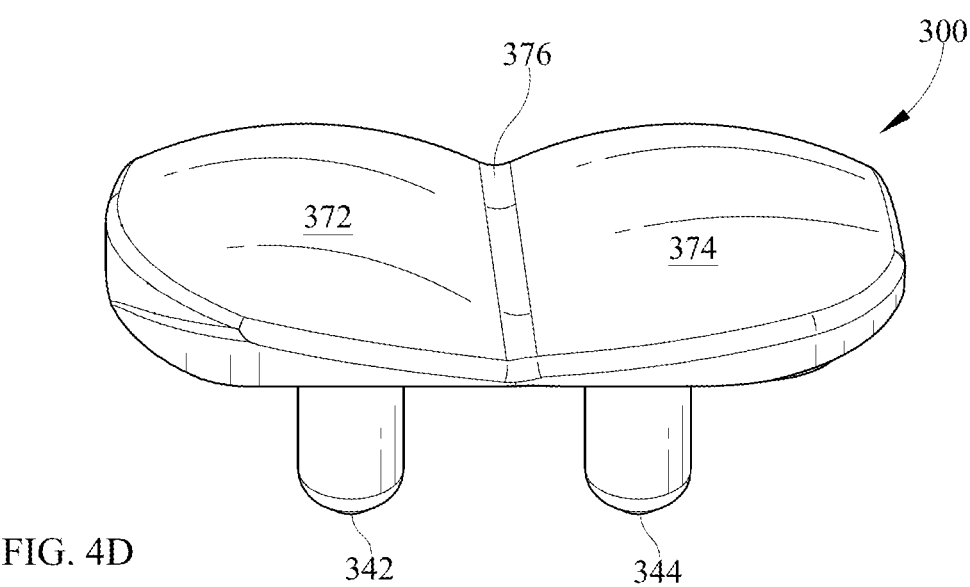
FIG. 4D is a frontal view of the talar implant of FIG. 4A.
Figure 4E:
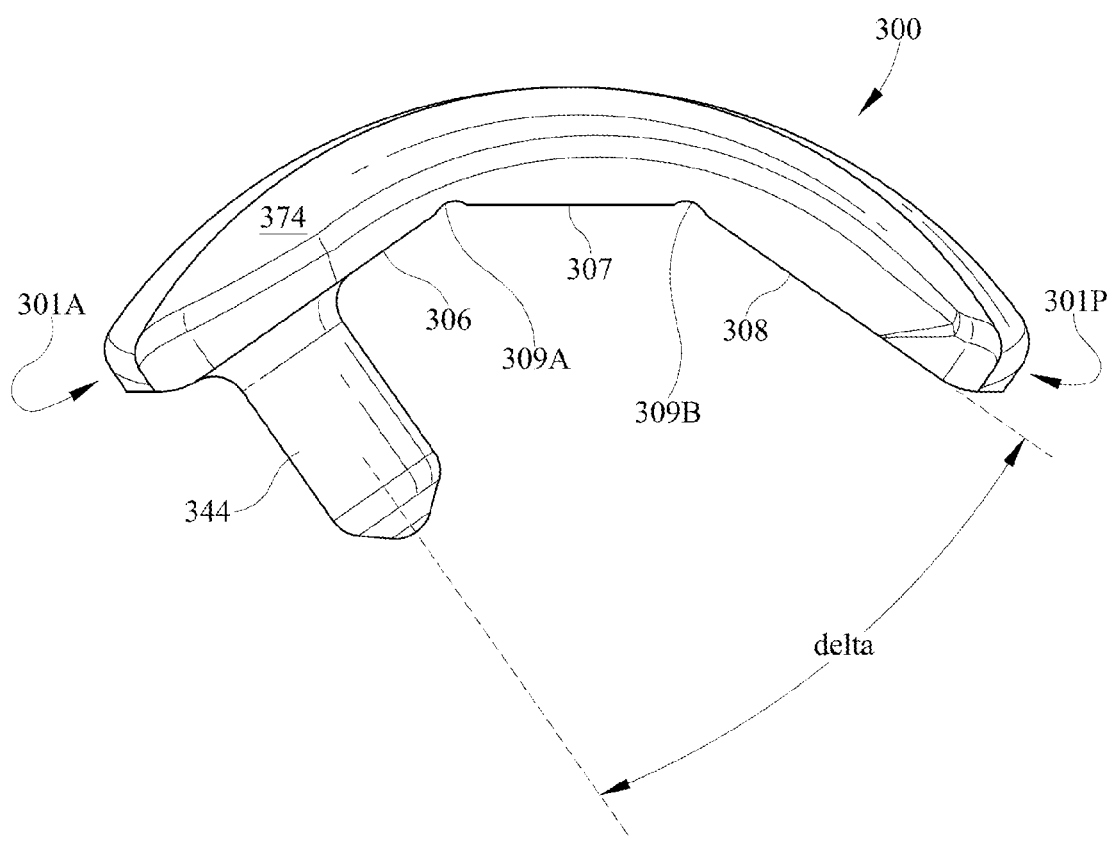
FIG. 4E is a side view of the talar implant of FIG. 4A.

The anterior talar-facing surface 306 may comprise one or more talar pegs. As illustrated, two talar pegs 342, 344 are provided. Talar pegs may be generally cylindrical with a rounded end. The shape of talar peg 342, 344 may be similar to the shape described for tibial pegs 142, 144. Each talar peg 342, 344 may comprise a piece of a sphere at the tip of the peg, followed by (tangent to) a cone, followed by a circular arc in revolution, followed by a cylinder. It is believed, although again it is not wished to be limited to this explanation, that such a shape of the tip of the talar peg 342, 344 may be helpful for similar reasons similar to those discussed in connection with the tibial pegs 142, 144. Talar pegs 342, 344 may each have a respective talar peg axis. The talar peg axis may have an angle delta, with respect to posterior talar planar surface 308, which is greater than zero as illustrated in FIG. 4E. Alternatively, talar pegs 342, 344 could be parallel to posterior talar planar surface 308. As illustrated and as is particularly visible in FIG. 4D, when viewed from the front (anterior), talar peg 342 is completely within the lateral range of condylar articulating surface 372 of talar implant 300, and talar peg 344 is completely within the lateral range of condylar articulating surface 374.

The articulating surface may comprise, as illustrated, two condyles, although other shapes are also possible. The first condylar articulating surface 372 and the second condylar articulating surface 374, as illustrated, may both be convex. However, in the region where the two condylar articulating surfaces approach each other, there may be a transition surface 376, which may be concave. As illustrated here and elsewhere herein, first condylar surface 372, second condylar surface 374 and transition surface 376 may all be formed by respective circular arcs being revolved around a common axis of revolution 399. Furthermore, as illustrated, the circular arc for first condylar surface 372 and the circular arc for second condylar surface 374 may have identical radii of curvature, although this is not essential. As illustrated, the circular arc for first condylar surface 372 and the circular arc for second condylar surface 374 both have a radius of curvature of 0.600 inch. As illustrated, transition surface 376 has a radius of curvature of 0.125 inch in the opposite sense from surfaces 372, 374. Variations from all of these dimensions would be possible.

Figure 4F:
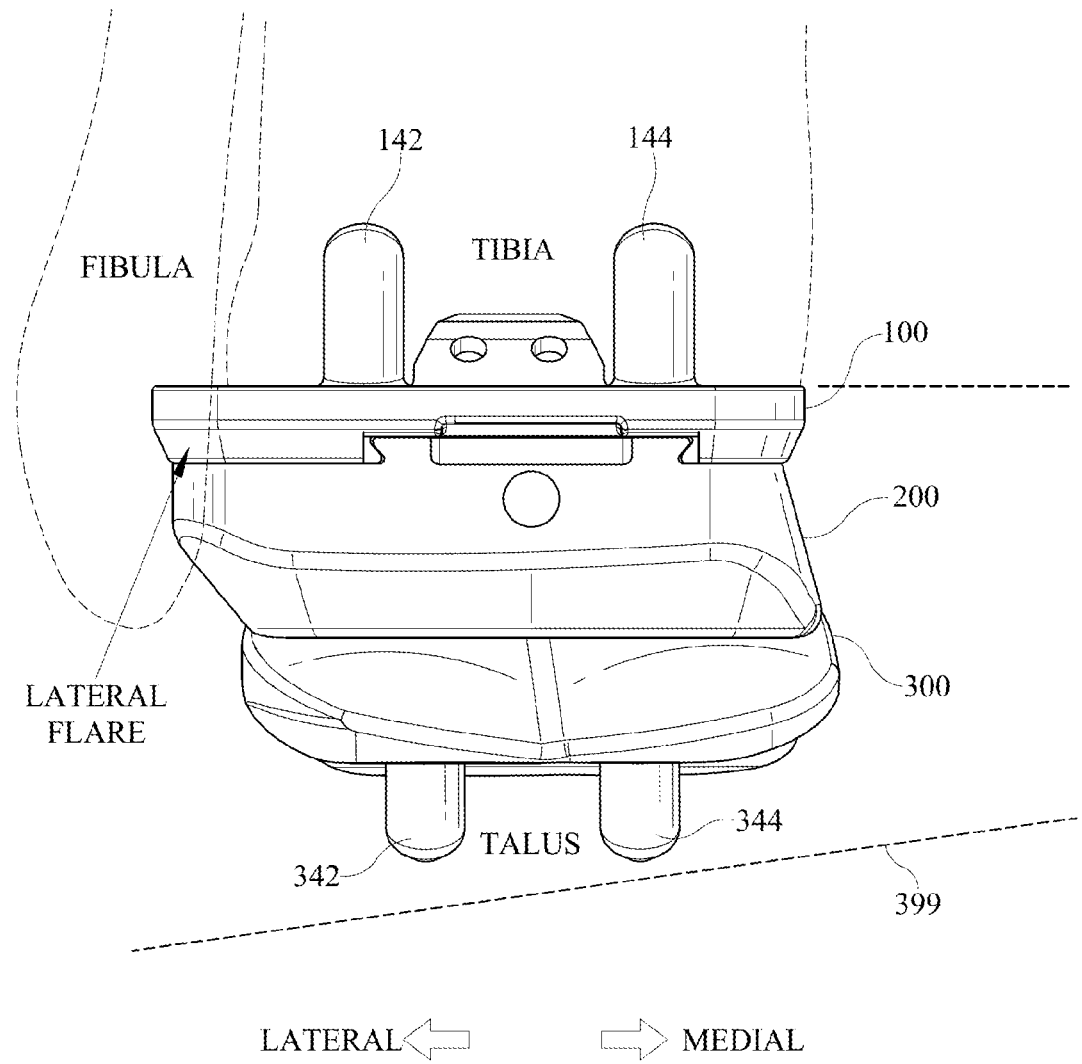
FIG. 4F is a frontal view of an implanted prosthesis, with the intermediate implant shown transparent, with certain anatomical features of the ankle also shown schematically.

FIG. 4F illustrates the assembled total ankle replacement prosthesis with respect to nearby anatomy of a patient's body. In particular, there is illustrated axis of revolution 399 for forming condylar surfaces 272, 274 and transition surface 276, and for forming condylar surfaces 372, 374 and transition surface 376. The orientation of axis of revolution 399 relative to the anatomy is also illustrated.

Referring now to FIG. 5A, intermediate implant 200 may have a tibial-implant-facing surface 102 and an opposed surface that is an articulating surface. The articulating surface may, as illustrated, be bicondylar, although other shapes are also possible. Condylar surface 272 of intermediate implant 200 may be generally concave and condylar surface 274 of intermediate implant 200 may be generally concave, and between them may be transition region 276, which may be convex. As illustrated, first condylar surface 272 may be a surface formed by a first circular arc 272A whose center 272C is indicated with a cross. Similarly, second condylar surface 274 may be a surface formed by a second circular arc 274A whose center 274C is similarly indicated. Similarly, surface 276 may be formed by another arc 276A whose center 276C is indicated. The axis of revolution may be the same for all of circular arcs 272A, 274A, and 276A. Furthermore, as illustrated, circular arcs 272A, 274A may have identical radii of curvature with each other, although this is not essential. The orientation of the axis of rotation may be non-horizontal, such as angled 8 degrees with respect to horizontal, as illustrated in FIGS. 4F and 5A.

Referring now to FIG. 5B, talar implant 300 may have a talus-facing surface 302 and an opposed surface that is an articulating surface. The articulating surface may, as illustrated, be bicondylar, although other shapes are also possible. Condylar surface 372 of talar implant 300 may be generally convex and condylar surface 374 of talar implant 300 may be generally convex, and between them may be transition region 376, which may be concave. As illustrated, first condylar surface 372 may be a surface formed by a first circular arc 372A whose center 372C is indicated with a cross. Similarly, second condylar surface 374 may be a surface formed by another arc 372A whose center 374C is indicated. Similarly, surface 376 may be formed by another arc 376A whose center 376C is indicated. The axis of revolution may be the same for all of circular arcs 372A, 374A, and 376A. Furthermore, as illustrated, circular arcs 372A, 374A may have identical radii of curvature with each other, although this is not essential. The orientation of the axis of rotation may be non-horizontal, such as for example it may be angled 8 degrees with respect to horizontal as illustrated in FIGS. 4F and 5B.

There may exist certain geometric relationships between the condylar surfaces of talar implant 300 and the condylar surfaces of intermediate implant 200. Specifically, the radii of curvature (illustrated as 0.820 inch) of the defining circular arcs 272A, 274A defining the concave condylar surfaces 272, 274 of the intermediate implant 200 may be larger than the corresponding radii of curvature (illustrated as 0.600 inch) of the defining circular arcs 372A, 374A defining the convex condylar surfaces 372, 374 of the talar implant 300. Also, the arc of the condylar surfaces 272, 274 in the intermediate implant 200 may extend over a larger distance or angular dimension than does the arc of the condylar surfaces 372, 374 in the talar implant 300, as can be seen by comparing FIGS. 5A and 5B.

It can be noted that it is not necessary for the talar-facing surface 272, 274, 276 of intermediate implant 200 and for the intermediate-implant-facing surface 372, 374, 376 of talar implant 300 to be bicondylar. Such surfaces could be unicondylar or even spherical, or other shape as appropriate. The respective shapes may be generally complementary to each other. As has been illustrated, the articulating surface of the intermediate implant 200 is mostly concave (272, 274) and the articulating surface of the talar implant 300 is mostly convex (372, 374). However, the opposite could be true instead. If surface 272 articulates with corresponding surface 372 and surface 274 illustrates with corresponding surface 374, it is not necessary for surface 276 to actually articulate with corresponding surface 376.

In regard to materials, the tibial implant 100 may be or may comprise a biocompatible metal. An example is titanium or a titanium alloy such as Ti-6Al-4V. Other biocompatible materials are also possible. In particular, the tibia-facing surface 102 of the tibial implant 100, and also fin 130 and pegs 142, 144 may comprise a material that is conducive to bone ingrowth or ongrowth, such as titanium or a titanium alloy. Such surface may be porous as desired to help promote bone ingrowth or ongrowth. If desired, some or all of the tibia-facing surface of the tibial implant 100 may be coated with a coating suitable to promote bone ingrowth or ongrowth. It is possible to use different materials in different places of any of these implants.

Further in regard to materials, the talar implant 300 may have any or all of the material characteristics just described for the tibial implant 100. If desired, some or all of the talus-facing surface of the talar implant 300, as well as talar pegs 342, 344, may be porous or may be coated with a coating suitable to promote bone ingrowth or ongrowth. It is possible to use different materials in different places of any of these implants.

Further in regard to materials, the intermediate implant 200 may comprise a biocompatible polymer. For example, ultra high molecular weight polyethylene may be used. The material may be chosen to have good wear characteristics against the corresponding material of talar implant 300. Other materials such as ceramic are also possible.

Further in regard to materials, it is possible that a ceramic material could be used for any of the components 100, 200, 300.

Figure 6A:
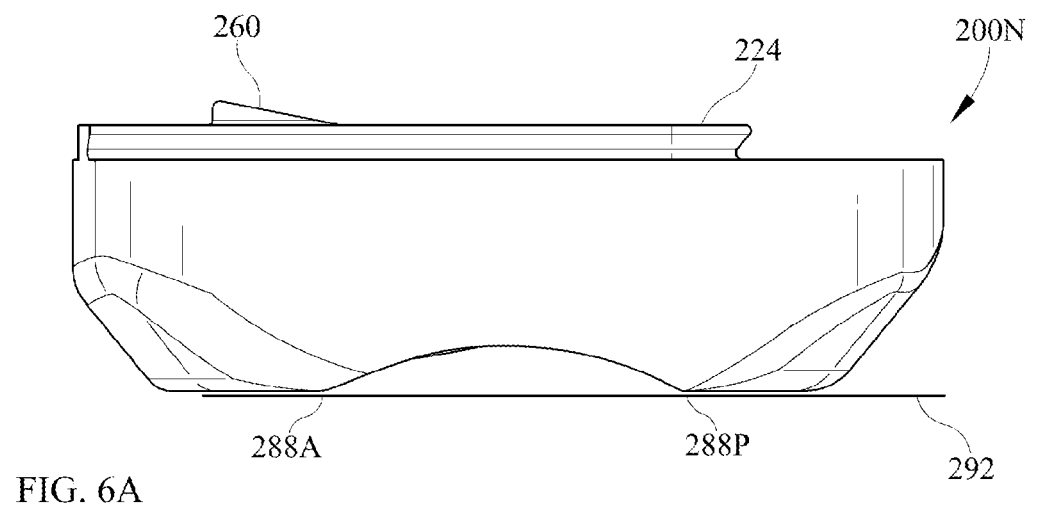
FIG. 6A is a side view of an intermediate implant similar to that of FIG. 3A, which may be referred to as a neutral intermediate implant.

Referring now to FIG. 6A, there is illustrated an intermediate implant 200N as was previously illustrated in FIG. 3C. This intermediate implant 200N illustrated in FIG. 6A is referred to as a neutral implant, as discussed here and elsewhere herein. In such an intermediate implant 200, the articulating talar condylar surfaces 272, 274 have an anterior edge 288A and a posterior edge 288P. At the anterior edge 288A, the talar-facing surface may end at or may blend into an anterior planar surface. Similarly, at the posterior edge 288P, the talar-facing surface may end at or may blend into a posterior planar surface. For a neutral intermediate implant 200, the anterior planar surface is coplanar with the posterior planar surface. More generally, for intermediate implant 200 geometries that are contoured at their lower ends in any manner that is more complicated than planar, there may be defined a midplane of the intermediate implant that is a vertical plane of symmetry midway between the dovetails 222, 224 is generally parallel to a sagittal plane in the anatomical sense, and in that midplane there may be defined a contact line 292 that touches but does not intersect the anterior portion of the lower surface of intermediate implant 200, and also touches but does not intersect the posterior portion of the lower surface of intermediate implant 200. Depending on details of geometry, either or both of those contact points could be in the form of the contact line being tangent to a curve, or could be the line overlapping with a planar surface, or could be the line touching a corner point. For a neutral intermediate implant 200N, the contact line 292 may be generally horizontal or parallel with the top surface 202 of intermediate implant 200.

Figure 6B:
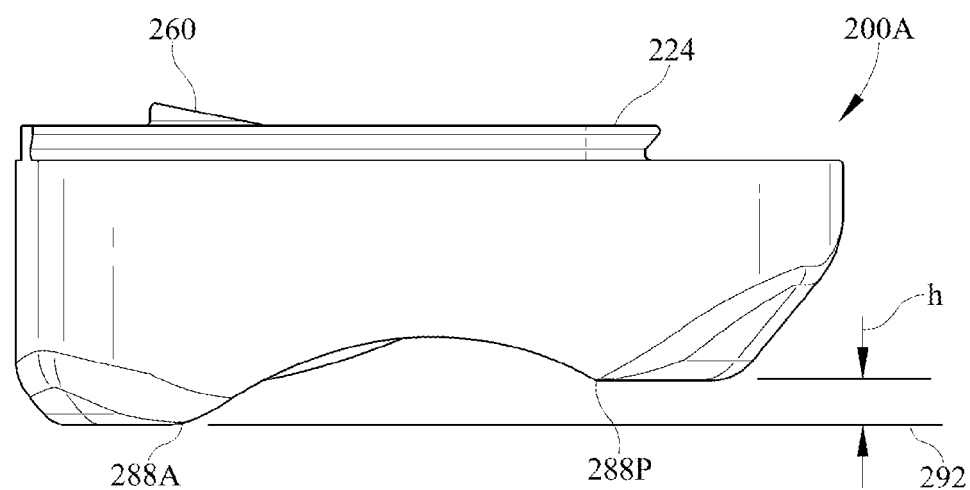
FIG. 6B is a side view of an intermediate implant that may be referred to as an anterior-biased intermediate implant.
Figure 6C:
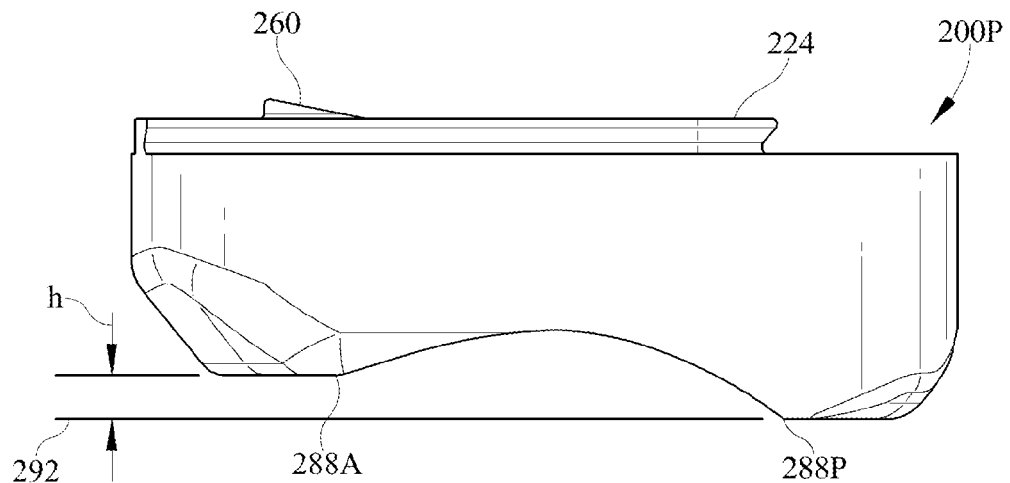
FIG. 6C is a side view of an intermediate implant that may be referred to as a posterior-biased intermediate implant.

As described, in certain embodiments of the invention, it is possible that there be an anterior edge 288A of the curved articulating surface of the intermediate implant 200 and a posterior edge 288P of the curved articulating surface of the intermediate implant 200, and it is possible that the anterior edge 288A and the posterior edge 288P might not be at the same elevation, with elevation measured from a reference plane, such as a top surface 202 of the intermediate implant 200. As shown in FIGS. 6A, 6B, and 6C, offset "h" shows a distance from contact line 292, which is conversely able to be measured from the top surface 202. In other words, the articulating curved surface of the intermediate implant 200 can extend farther (FIG. 6B) anteriorly than it does posteriorly, or, alternatively, the articulating curved surface of the intermediate implant 200 can extend farther posteriorly (FIG. 6C) than it does anteriorly. It is possible that the use of unequal anterior and posterior angular extents of the articulating surfaces, or the unequal elevational positions of the corresponding endpoints of the articulating surfaces, could decrease the likelihood of subluxation in particular directions, as discussed elsewhere herein. This is illustrated in FIG. 6B for an anterior-biased intermediate implant 200A, and in FIG. 6C for a posterior-biased intermediate implant 200P. If the anterior edge 288A extends farther than the posterior edge 288P as in FIG. 6B, this may reduce the likelihood of subluxation of the talus in the anterior direction relative to the tibia. If the posterior edge 288P extends further than the anterior edge 288A as in FIG. 6C, this may reduce the likelihood of subluxation of the talus in the posterior direction relative to the tibia. If the extent of the curved articulating surface were to be extended equally in both directions (anterior and posterior), this might discourage subluxation in both the anterior and the posterior directions, but it would not discourage one direction of subluxation preferentially compared to the other direction of subluxation, and this could be expected to make it generally harder to bring intermediate implant 200 into the surgical site into its intended place, requiring greater stretching or displacement of nearby tissues and anatomical features. In particular, if the arc length of the articulating surface of intermediate implant 200A is extended in the anterior direction but not the posterior, and if this intermediate implant 200A is inserted surgically from the anterior-to-posterior direction after the tibial implant 100 and the talar implant 300 have already been implanted, this would not increase the difficulty of inserting the intermediate implant 200A, but it would provide greater protection against subluxation in the form of the foot or the talus subluxing or moving in an anterior direction with respect to the tibia.

The anterior bias intermediate implant 200A may make it especially unlikely or difficult for subluxation to occur in the sense of the foot and talus subluxing in an anterior direction relative to the tibia. The posterior bias intermediate implant 200P may make it especially unlikely or difficult for subluxation to occur in the sense of the foot and talus subluxing in a posterior direction relative to the tibia.

It is possible that a kit may be provided that includes more than one type of implant, such as a neutral implant 200N, an anterior bias intermediate implant 200A and a posterior bias intermediate implant 200P. Each of those intermediate implants 200N, 200A, 200P may fit or be attachable to the same tibial implant 100. In this way, a surgeon can choose to use any of the various intermediate implants 200N, 200A, 200P as appropriate, while the tibial implant 100 and the talar implant 300 are unaffected by the choice of intermediate implant 200. The choice may be made based at least in part on the anatomy of the patient and the likelihood of any factors that might contribute to occurrence of subluxation. It would also be possible that a kit contain more than one neutral intermediate implant 200N, with varying extents of arc. A neutral intermediate implant having a larger extent of arc in both front and rear directions would provide more protection against subluxation in both directions, although it could be more difficult to insert, in the sense of requiring greater stretching of surrounding tissues.

Further, in terms of a kit, any or all of the described components may be provided in mirror image versions corresponding to the left and right sides of a patient's body. Also, any or all components may be provided in multiple sizes.

In terms of surgical procedure and use of the described apparatus, a typical procedure is described here. It is to be understood that variations in the sequence of steps are possible. First, access to the ankle may be performed from the anterior of the ankle. A fixture may be anchored to the patient's leg externally to aid in determination of position of cuts. A cutting guide may be used to direct an oscillatory saw to remove the distal portion of the tibia. Working at an angle, possibly with a right-angle drill, drilling or other bone removal may be performed to the cut surface of the tibia such as to prepare for the pegs and the fin. For the assumed surgical access from the anterior direction, it may easier to drill trial holes for the tibial pegs 142, 144 in the tibia, and it may be more difficult to prepare the space for the fin 130 because the fin location is deeper within the surgical site. The tibial implant 100 may be put into the surgical site, and may be hammered or urged in a posterior direction into its final position. So, the sharp end of the fin 130 may be advantageous in that the sharp end can force its own way into the tibial bone to some extent, as may be needed, upon application of force to the anterior end of the tibial implant 100 in a posterior direction. The fin 130 may help to prevent the posterior portion of tibial implant 100 from separating from the tibia upon certain motions by the patient.

The talus can be prepared by cutting a series of flats into its surface, corresponding to the underside surface of talar implant 300. Holes can be drilled corresponding to talar pegs 342, 344. The talar implant 300 can be urged into place.

After the tibial implant 100 and the talar implant 300 have been implanted, the intermediate implant 200 may be slid into place. Intermediate implant 200 may be tapped or urged in a posterior direction until it engages with tibial implant 100.

The preceding description is provided to enable a person of ordinary skill in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. An ankle replacement prosthesis, comprising:
    a tibial implant for implanting onto a tibia having a tibial-facing surface and a tibial implant lower surface opposite said tibial-facing surface and having an anterior end and a posterior end;
    a talar implant for implanting onto a talus having a talar-facing surface and a talar implant upper surface opposite said talar-facing surface and having an anterior end and a posterior end; and
    an intermediate implant having an anterior end and a posterior end and a tibial-facing surface and a talar-facing surface, said intermediate implant fitting between said tibial implant and said talar implant,
    wherein said tibial-facing surface of said intermediate implant fixedly attaches to said tibial implant and said talar-facing surface of said intermediate implant has an articulating surface that articulatingly engages said talar implant, wherein said intermediate implant has a first edge of said articulating surface at an anterior end thereof and a second edge of said articulating surface at a posterior end thereof, wherein said first edge is at a different elevation than said second edge, with elevation being defined with respect to a top surface of said intermediate implant;

wherein said tibial-facing surface further comprises a fin located closer to said posterior end of said tibial implant than said anterior end of said tibial implant, said fin having a proximal fin end attached to said tibial-facing surface and having a distal fin end depending from said tibial-facing surface at a fin angle measured from said tibial-facing surface;

wherein said tibial-facing surface further comprises at least one peg located closer to said anterior end of said tibial implant than said fin is located, said at least one peg having a proximal peg end attached to said tibial-facing surface and having a distal peg end depending from said tibial-facing surface at a peg angle measured from said tibial-facing surface; and wherein said peg further comprises a tip portion constituting a portion of a sphere followed by a portion of a cone followed by a surface formed by a circular arc in revolution around a longitudinal axis followed by a cylindrical surface.

2. The prosthesis of claim 1, wherein said first edge is more distal than said second edge to said top surface.

3. The prosthesis of claim 1, wherein said first edge is more proximal than said second edge to said top surface.

4. The prosthesis of claim 1, wherein said tibial implant lower surface further comprises a cutout region therein having a cutout boundary therearound with first, second, and third boundary sides thereof.

5. The prosthesis of claim 4, wherein said cutout region is in communication with a tibial implant entrance region at said anterior end of said tibial implant.

6. The prosthesis of claim 5, wherein first and second boundary sides each further comprises a cutout dovetail.

7. The prosthesis of claim 1, wherein said fin angle is between zero and ninety degrees.

8. The prosthesis of claim 7, wherein said fin angle is between twenty and seventy degrees.

9. The prosthesis of claim 4, wherein said fin proximal end is located on said tibial-facing surface opposite to and entirely within said cutout boundary of said cutout region of said tibial implant lower surface.

10. The prosthesis of claim 1, wherein said peg angle is between zero and ninety degrees.

11. The prosthesis of claim 10, wherein said peg angle is between twenty and seventy degrees.

12. The prosthesis of claim 1, wherein said peg angle is different from said fin angle.

13. The prosthesis of claim 1, wherein said tibial implant comprises an external shape that closely matches a shape of a prepared end of a lower tibia when viewed in a transverse plane at a lower portion of a tibia.

14. The prosthesis of claim 6, wherein said tibial-facing surface of said intermediate implant further comprises a projection thereon.

15. The prosthesis of claim 14, wherein said projection further comprises a dovetail configuration complementary to said cutout dovetail.

16. The prosthesis of claim 15, wherein said intermediate implant further comprises an intermediate implant recess on an anterior edge thereof.

17. The prosthesis of claim 16, wherein one of said tibial implant and said intermediate implant comprises a pocket and the other of said tibial implant and said intermediate implant comprises a latch, said latch and said pocket engaging with each other upon assembly, and wherein, when viewed along an anterior-posterior direction, said intermediate implant recess at least partially overlaps with said pocket and said latch.

18. The prosthesis of claim 6, wherein said articulating surface further comprises a bi-condylar surface.

19. The prosthesis of claim 18, wherein said bi-condylar surface further comprises first and second concave condylar surfaces each formed by respective circular arcs revolved around an axis of revolution.

20. The prosthesis of claim 19, where said axis of revolution is disposed at an angle of approximately eight degrees measured from a plane containing said tibial-facing surface of said tibial implant.

21. A tibial implant comprising:
an outer perimeter such that, upon proceeding counter-clockwise around said perimeter as viewed from above along a vertical axis, said outer perimeter further comprises a first straight edge;
said first straight edge being followed by a first convex corner that meets and is tangent to said first straight edge;
said first convex corner being followed by a second straight edge or shallow arc that meets and is tangent to said first convex corner,
wherein an angle of said first convex corner is greater than 90 degrees but less than 180 degrees;
said second straight edge or said shallow arc being followed by a second convex corner that meets and is tangent to said second straight edge or said shallow arc;
said second convex corner being followed by a first concave curve, wherein said second convex corner transitions to said first concave curve at a first inflection point;
wherein there is a tangent line that is parallel to said first straight edge and is tangent to second convex corner at a tangency point that is farther from said first straight edge than is said first inflection point;
wherein said first concave curve continues on from said first inflection point to cross said tangent line so as to become farther from said first straight edge than is said tangent line; and
wherein said first concave curve is followed by a convex curve that proceeds from said first concave curve and returns to said first straight edge to form a complete perimeter of said tibial implant.

22. A tibial implant of claim 21, wherein said tibial implant has a tibia-facing surface and a lower surface opposed to said tibia-facing surface,
wherein said lower surface has a cutout region extending in from said outer perimeter of said tibial implant, said cutout region defined by a cutout perimeter shape that demarcates said cutout region from a remainder of said lower surface of said tibial implant, and
wherein said cutout perimeter shape has a tibial dovetail configuration.

23. The tibial implant of claim 22, wherein said tibial dovetail configuration extends along a first side and a second side and at least a portion of a remainder of said cutout perimeter.

24. The tibial implant of claim 23, wherein said first side and said second side are parallel to each other.

25. The tibial implant of claim 21, in combination with a talar implant and an intermediate implant;
- wherein said tibial implant for implanting onto a tibia includes a tibial-facing surface and a tibial implant lower surface opposite said tibial-facing surface and having an anterior end and a posterior end;
- wherein said talar implant for implanting onto a talus includes a talar-facing surface and a talar implant upper surface opposite said talar-facing surface and having an anterior end and a posterior end; and
- wherein said intermediate implant includes an anterior end and a posterior end and a tibial-facing surface and a talar-facing surface, said intermediate implant fitting between said tibial implant and said talar implant.

26. The tibial implant of claim 25, wherein said tibial-facing surface of said intermediate implant fixedly attaches to said tibial implant and said talar-facing surface of said intermediate implant has an articulating surface that articulatingly engages said talar implant.

27. The tibial implant of claim 26, wherein said intermediate implant has a first edge of said articulating surface at an anterior end thereof and a second edge of said articulating surface at a posterior end thereof,
- wherein said first edge is at a different elevation than said second edge, with elevation being defined with respect to a top surface of said intermediate implant.

28. The tibial implant of claim 25, wherein said tibial-facing surface further comprises a fin located closer to said posterior end of said tibial implant than said anterior end of said tibial implant, said fin having a proximal fin end attached to said tibial-facing surface and having a distal fin end depending from said tibial-facing surface at a fin angle measured from said tibial-facing surface.

29. The tibial implant of claim 28, wherein said tibial-facing surface further comprises at least one peg located closer to said anterior end of said tibial implant than said fin is located, said at least one peg having a proximal peg end attached to said tibial-facing surface and having a distal peg end depending from said tibial-facing surface at a peg angle measured from said tibial-facing surface.

* * * * *